(12) United States Patent
Howard, Jr. et al.

(10) Patent No.: US 9,748,497 B2
(45) Date of Patent: Aug. 29, 2017

(54) ELECTRONIC DEVICE INCLUDING A DIAZACHRYSENE DERIVATIVE

(71) Applicant: E.I. DU PONT DE NEMOURS AND COMPANY, Wilmington, DE (US)

(72) Inventors: Michael Henry Howard, Jr., Montchanin, DE (US); Denis Yurievich Kondakov, Wilmington, DE (US); Weiying Geo, Landenberg, PA (US); Steven Kit Chow, Brooklyn, DE (US); Adam Fennimore, Wilmington, DE (US); Norman Herron, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 157 days.

(21) Appl. No.: 14/768,100

(22) PCT Filed: Feb. 20, 2014

(86) PCT No.: PCT/US2014/017238
§ 371 (c)(1),
(2) Date: Aug. 14, 2015

(87) PCT Pub. No.: WO2014/130597
PCT Pub. Date: Aug. 28, 2014

(65) Prior Publication Data
US 2015/0380664 A1    Dec. 31, 2015

Related U.S. Application Data

(60) Provisional application No. 61/768,852, filed on Feb. 25, 2013.

(51) Int. Cl.
*H01L 51/00*     (2006.01)
*C09K 11/02*     (2006.01)
(Continued)

(52) U.S. Cl.
CPC ........ *H01L 51/0072* (2013.01); *C07D 471/04* (2013.01); *C09K 11/025* (2013.01);
(Continued)

(58) Field of Classification Search
None
See application file for complete search history.

(56) References Cited

U.S. PATENT DOCUMENTS 6,670,645 B2    12/2003    Grushin et al.
6,875,524 B2    4/2005    Hatwar et al.
(Continued)

FOREIGN PATENT DOCUMENTS

WO    03/040257 A1    5/2003
WO    03/063555 A1    7/2003
(Continued)

OTHER PUBLICATIONS

CRC Handbook of Chemistry & Physics, 81$^{st}$ Edition, (2000-2001)—Book Not Included.
(Continued)

*Primary Examiner* — J. L. Yang

(57) ABSTRACT

There is provided a compound having Formula I

Formula I (Continued)

In Formula I: $R^1$-$R^{10}$ are the same or different and can be H, D, alkyl, aryl, alkoxy, aryloxy, silyl, or deuterated analogs of alkyl, aryl, alkoxy, aryloxy and silyl, where adjacent R groups can be joined together to form a ring; and all other sites are H or D. Additionally in Formula I: (i) at least one of $R^1$-$R^3$ and at least one of $R^4$-$R^6$ is alkyl, alkoxy, silyl, or a deuterated analog, and (ii) at least one of $R^1$-$R^3$ and at least one of $R^4$-$R^6$ is aryl, aryloxy, or a deuterated analog.

14 Claims, 2 Drawing Sheets

(51) Int. Cl.
*C07D 471/04* (2006.01)
*C09K 11/06* (2006.01)
*H01L 51/50* (2006.01)

(52) U.S. Cl.
CPC .......... C09K 11/06 (2013.01); H01L 51/0067 (2013.01); *C09K 2211/1011* (2013.01); *H01L 51/5012* (2013.01); *H01L 51/5072* (2013.01); *H01L 2251/308* (2013.01)

(56) References Cited

U.S. PATENT DOCUMENTS

| | | |
|---|---|---|
| 2004/0102577 A1 | 5/2004 | Hsu et al. |
| 2004/0127637 A1 | 7/2004 | Hsu et al. |
| 2005/0158577 A1 | 7/2005 | Ishibashi et al. |
| 2005/0205860 A1 | 9/2005 | Hsu et al. |
| 2007/0063638 A1 | 3/2007 | Tokairin et al. |
| 2007/0292713 A9 | 12/2007 | Dobbs et al. |
| 2013/0099206 A1* | 4/2013 | Jung .................. C07D 471/04 257/40 |

FOREIGN PATENT DOCUMENTS

| | | |
|---|---|---|
| WO | 2004/016710 A1 | 2/2004 |
| WO | 2007/021117 A1 | 2/2007 |
| WO | 2009/018009 A1 | 2/2009 |
| WO | 2011/053334 A1 | 5/2011 |
| WO | 2012/082593 A2 | 6/2012 |

OTHER PUBLICATIONS

Kirk—Othmer Encyclopedia of Chemical Technology, 4$^{th}$ Edition, Vol. 18, pp. 837-860, 1996, Y. Wang—Book Not Included.
Markus, John, Electronics & Nucleonics Dictionary, pp. 470 & 476, Mc Graw-Hill, Inc., 1966—Book Not Included.
G. R. Newkome & W.W. Paudler, Contemporary Heterocyclic Chemistry, (NY: John Wiley & Sons), 1982, Chapter 15.1.2—Book Not Included.
G. Gustafsson, Y. Cao, G.M. Treacy, F. Klavetter, N. Colaneri, A.J. Heeger, "Flexible Light-Emitting Diodes Made From Soluble Conducting Polymers", Nature, Vol. 357, pp. 477-479, Jun. 11, 1992.

* cited by examiner

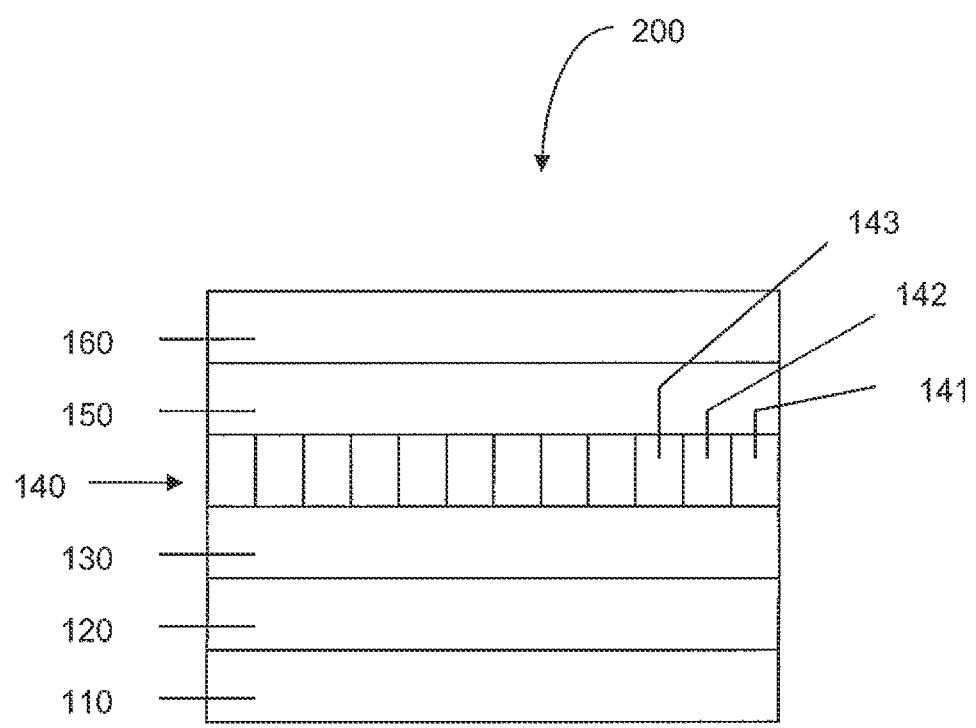

ELECTRONIC DEVICE INCLUDING A DIAZACHRYSENE DERIVATIVE

RELATED APPLICATION DATA

This application claims priority under 35 U.S.C. §110(e) from U.S. Provisional Application No. 61/768,852, filed on Feb. 25, 2013, which is incorporated by reference herein in its entirety.

BACKGROUND INFORMATION

Field of the Disclosure

This disclosure relates in general to electroactive diazachrysene compounds. It also relates to organic electronic devices including at least one layer having a diazachrysene derivative.

Description of the Related Art

In organic photoactive electronic devices, such as organic light emitting diodes ("OLED"), that make up OLED displays, the organic electroactive layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the electroactive component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for new materials for electronic devices.

SUMMARY

There is provided a diazachrysene derivative having Formula I

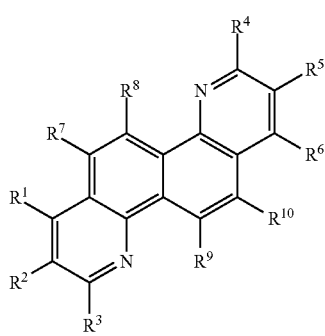

Formula I wherein:
R$^1$-R$^{10}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring;
with the proviso that (i) at least one of R$^1$-R$^3$ and at least one of R$^4$-R$^6$ is selected from the group consisting of alkyl, alkoxy, silyl, and deuterated analogs thereof, and (ii) at least one of R$^1$-R$^3$ and at least one of R$^4$-R$^6$ is selected from the group consisting of aryl, aryloxy, and deuterated analogs thereof.

There is also provided a composition comprising (a) a host compound having Formula I and (b) a dopant capable of electroluminescence having an emission maximum between 380 and 750 nm.

There is also provided an electronic device comprising at least one layer comprising the compound of Formula I.

There is also provided an electronic device comprising at least one electroactive layer positioned between two electrical contact layers, wherein the at least one electroactive layer of the device includes an electroactive compound having Formula I.

There is also provided an organic electronic device comprising an anode, a hole injection layer, a photoactive layer, an electron transport layer, and a cathode, wherein at least one of the photoactive layer and the electron transport layer comprises a compound having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 2 includes a schematic diagram of another example of an organic electronic device.

Figure 1:
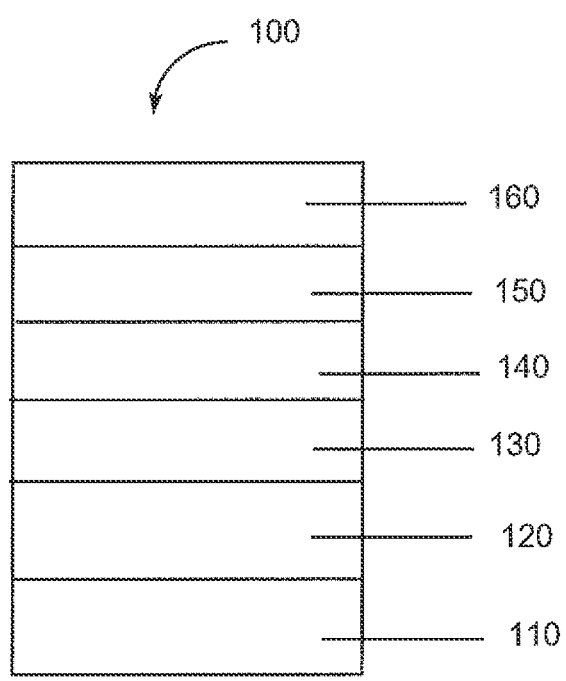
FIG. 1 includes a schematic diagram of an example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Diazachrysene Derivatives, the Electroactive Composition, the Electronic Device, and finally Examples.

1. DEFINITIONS AND CLARIFICATION OF TERMS

Before addressing details of embodiments described below, some terms are defined or clarified.

The term "alkyl" is intended to mean a group derived from an aliphatic hydrocarbon. In some embodiments, alkyl groups have 1-20 carbons.

The term "aryl" is intended to mean a group derived from an aromatic compound. The term "aromatic compound" is intended to mean an organic compound comprising at least one unsaturated cyclic group having delocalized pi electrons. The term is intended to encompass both hydrocarbon aromatic compounds having only carbon and hydrogen atoms, and heteroaromatic compounds wherein one or more of the carbon atoms within the cyclic group has been replaced by another atom, such as nitrogen, oxygen, sulfur, or the like. In some embodiments, hydrocarbon aryl groups have 6-60 ring carbons. In some embodiments, heterocyclic aryl groups have 3-60 ring carbons.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although photoactive materials may also have some charge transport properties, the term "charge transport layer, material, member, or structure" is not intended to include a layer, material, member, or structure whose primary function is light emission or light reception.

The term "deuterated" is intended to mean that at least one hydrogen has been replaced by deuterium (abbreviated herein as "D"). The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, insulating materials and environmental barrier materials.

The term "host material" is intended to mean a material, usually in the form of a layer, to which a dopant may or may not be added. The host material may or may not have electronic characteristic(s) or the ability to emit, receive, or filter radiation.

The term "hydrocarbon aryl" is intended to mean an aryl group containing only hydrogen and carbon atoms.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The terms "N-heterocycle" and "N-heteroaryl" refer to a heteroaromatic compound or heteroaromatic group, respectively, having at least one nitrogen in an aromatic ring.

The term "organic electronic device," or sometimes just "electronic device," is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector or photovoltaic cell).

Unless otherwise indicated, all groups can be unsubstituted or substituted. Unless otherwise indicated, all groups can be linear, branched or cyclic, where possible. In some embodiments, the substituents are selected from the group consisting of alkyl, alkoxy, aryl, silyl, and deuterated analogs thereof.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, $81^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. DIAZACHRYSENE DERIVATIVES

Electron transport materials have been used as host materials in photoactive layers and in electron transport layers. Electron transport materials based on metal complexes of quinoline ligands, such as with Al, Ga, or Zr, have been used in these applications. However, there are several disadvantages. The complexes can have poor atmospheric stability when used as hosts. It is difficult to plasma clean fabricated parts employing such metal complexes. The low triplet energy leads to quenching of phosphorescent emission of >2.0 eV energy.

In some embodiments, the diazachrysene derivatives described herein have higher triplet energies and are suitable as hosts for phosphorescent emitters. As used herein, the term "diazachrysene derivative" is intended to mean a compound having at least one substituted diazachrysene group structure within the compound, where the 4,10-diazachrysene group structure is shown below.

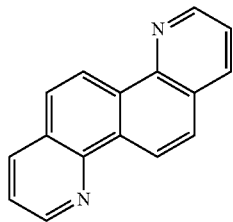 [SMILES: c1cnc2c(c1)ccc1c2ccc2cccnc21]

In some embodiments, the diazachrysene derivatives of Formula I are useful as solution processible electron dominated hosts for OLED devices.

In some embodiments, the diazachrysene derivatives of Formula I are useful as electron transport materials.

In some embodiments, the diazachrysene derivatives of Formula I are useful as electron transport materials suitable for n-doping in OLED devices having a thick electron transport layer.

In some embodiments, devices made with the diazachrysene derivatives of Formula I have lower operating voltage.

In some embodiments, devices made with the diazachrysene derivatives of Formula I have higher efficiency.

In some embodiments, devices made with the diazachrysene derivative of Formula I have longer lifetimes.

In some embodiments, the materials are useful in any printed electronics applications.

In some embodiments, the materials are useful in photovoltaics.

In some embodiments, the materials are useful in TFTs.

In some embodiments, the compound having Formula I is deuterated. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

The diazachrysene derivative compounds described herein have Formula I

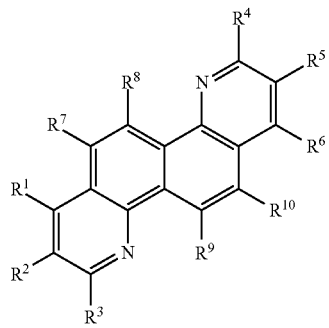

Formula I wherein:
$R^1$-$R^{10}$ are the same or different and are selected from the group consisting of H, D, alkyl, aryl, silyl, and deuterated analogs of alkyl, aryl, and silyl, where adjacent R groups can be joined together to form a ring;
with the proviso that (i) at least one of $R^1$-$R^3$ and at least one of $R^4$-$R^6$ is selected from the group consisting of alkyl, silyl, and deuterated analogs thereof, and (ii) at least one of $R^1$-$R^3$ and at least one of $R^4$-$R^6$ is aryl or deuterated aryl.

As used herein, "adjacent R groups" refers to R groups on carbons that are joined together with a single or multiple bond. Thus, in Formula I, $R^1$ and $R^2$ are adjacent R groups, as are $R^2$ and $R^3$, $R^4$ and $R^5$, $R^5$ and $R^6$, $R^7$ and $R^8$, and $R^9$ and $R^{10}$.

In some embodiments, adjacent R groups form an aliphatic ring. In some embodiments the aliphatic ring has 5-8 carbons.

In some embodiments, adjacent R groups form a 5- or 6-membered aromatic ring. In some embodiments, there are no heteroatoms in the aromatic ring.

When two of $R^1$-$R^3$ or $R^4$-$R^6$ are joined to form an aromatic ring, the third group of $R^1$-$R^3$ and $R^4$-$R^6$ is selected from the group consisting of alkyl, alkoxy, silyl, and deuterated analogs thereof.

When two of $R^1$-$R^3$ or $R^4$-$R^6$ are joined to form an aliphatic ring, the third group of $R^1$-$R^3$ and $R^4$-$R^6$ is selected from the group consisting of aryl, aryloxy, and deuterated analogs thereof.

In some embodiments, one of $R^1$-$R^3$ and one of $R^4$-$R^6$ is H or D.

In some embodiments, two of $R^1$-$R^3$ and two of $R^4$-$R^6$ are aryl groups or deuterated aryl groups.

In some embodiments, two of $R^1$-$R^3$ and two of $R^4$-$R^6$ are aryloxy groups or deuterated aryloxy groups.

In some embodiments, two of $R^1$-$R^3$ and two of $R^4$-$R^6$ are alkyl groups or deuterated alkyl groups.

In some embodiments, two of $R^1$-$R^3$ and two of $R^4$-$R^6$ are alkoxy groups or deuterated alkoxy groups.

In some embodiments, two of $R^1$-$R^3$ and two of $R^4$-$R^6$ are silyl groups or deuterated silyl groups.

In some embodiments, there are no amino groups.

In some embodiments, there are no carbazolyl groups.

In some embodiments, at least one of $R^1$-$R^3$ is an aryl group having Formula a Formula a where:
- $R^1$ is the same or different at each occurrence and is selected from the group consisting of D, alkyl, alkoxy, aryl, aryloxy, silyl, diarylamino, deuterated alkyl, deuterated alkoxy, deuterated aryl, deuterated aryloxy, deuterated silyl, and deuterated diarylamino;
- a is the same or different at each occurrence and is an integer from 0-4;
- b is an integer from 0-5; and
- m is an integer from 1 to 5.

In some embodiments, at least one of $R^1$-$R^3$ is an aryl group having Formula b Formula b where R' and m are as defined above. The group with Formula b may also be deuterated.

In some embodiments, of Formula a and Formula b, m is 1-2.

In some embodiments, at least one of $R^1$-$R^3$ is an aryl group having Formula c Formula c where R' is as defined above. The group with Formula c may also be deuterated.

In some embodiments of Formulae a-c, R' is not an amino group.

In some embodiments of Formulae a-c, R' is selected from the group consisting of alkyl, aryl, silyl, and deuterated analogs thereof.

In some embodiments, at least one of $R^4$-$R^6$ is aryl having Formula a, as defined above.

In some embodiments, at least one of $R^4$-$R^6$ is aryl having Formula b, as defined above.

In some embodiments, at least one of $R^4$-$R^6$ is aryl having Formula c, as defined above.

In some embodiments, at least one of $R^1$-$R^3$ is an aryl group and includes a heteroaryl or deuterated heteroaryl group. The heteroaryl or deuterated heteroaryl group may be bonded directly to the diazachrysene core, or may be bonded to another aryl group.

In some embodiments, at least one of $R^4$-$R^6$ is an aryl group and includes a heteroaryl or deuterated heteroaryl group.

In some embodiments, the heteroaryl group is an N-heteroaryl or deuterated N-heteroaryl group. In some embodiments, the N-heteroaryl or deuterated N-heteroaryl group is selected from the group consisting of pyridyl, pyrimidinyl, pyrazinyl, pyridazinyl, triazinyl, quinolinyl, isoquinolinyl, quinoxalinyl, naphthyridinyl, imidazolyl, pyrazolyl, benzodiazolyl, carbazolyl, and deuterated analogs thereof.

Examples of N-heteroaryl groups include, but are not limited to, those shown below.

where Y is an aryl group, deuterated aryl group, or a point of attachment. The group can be bonded at any of the positions available. Deuterated analogs of the above groups may also be used.

In some embodiments, at least one of $R^1$-$R^3$ and at least one of $R^4$-$R^6$ is selected from the group consisting of

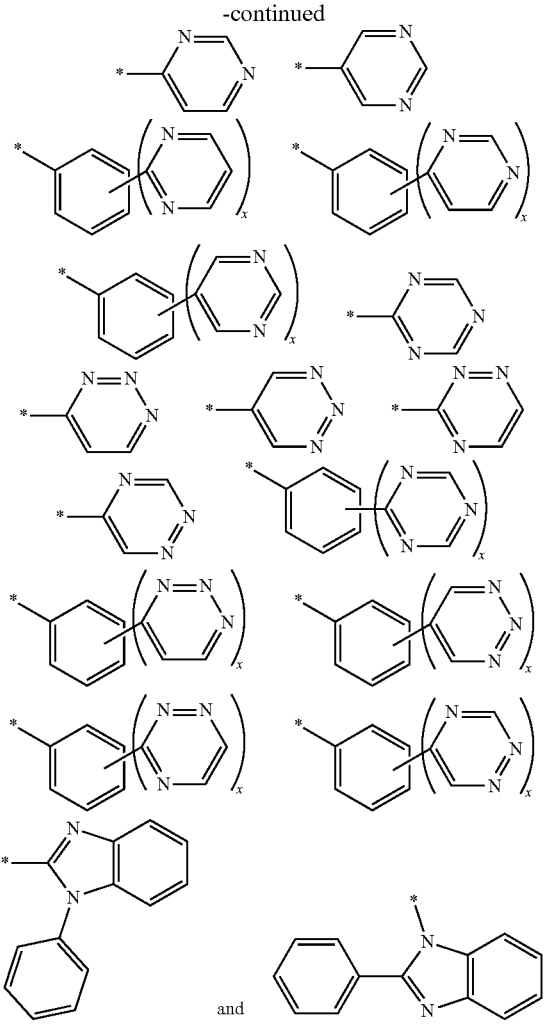

where x=1 or 2, the asterisk indicates the point of attachment to the compound, and positions available for H can be H or D.

In some embodiments, at least one of $R^1$-$R^3$ and at least one of $R^4$-$R^6$ is an alkyl group or deuterated alkyl having 1-12 carbons; in some embodiments, 1-8 carbons; in some embodiments, 1-5 carbons.

In some embodiments, at least one of $R^7$-$R^{10}$ is an aryl group.

In some embodiments, at least one of $R^7$-$R^{10}$ is aryl having Formula a, as defined above.

In some embodiments, at least one of $R^7$-$R^{10}$ is aryl having Formula b, as defined above.

In some embodiments, at least one of $R^7$-$R^{10}$ is aryl having Formula c, as defined above.

In some embodiments, at least one of $R^7$-$R^{10}$ is a heteroaryl or deuterated heteroaryl group. In some embodiments, the heteroaryl group is an N-heteroaryl or deuterated N-heteroaryl group.

In some embodiments, at least one of $R^7$-$R^{10}$ is an alkyl group or deuterated alkyl group. In some embodiments, the alkyl group or deuterated alkyl group has 1-12 carbons; in some embodiments, 1-8 carbons; in some embodiments, 1-5 carbons.

In some embodiments, each of $R^7$-$R^{10}$ is H or D.

In some embodiments, the diazachrysene derivatives have Formula I(a)

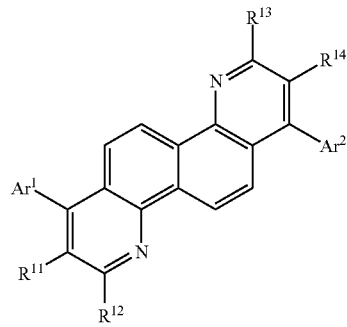

Formula I(a)

wherein:
Ar$^1$ and Ar$^2$ are the same or different and are selected from the group consisting of aryl, aryloxy, and deuterated analogs thereof;
$R^{11}$-$R^{14}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring; and
all other sites are H or D;
with the proviso that at least one of $R^{11}$ and $R^{12}$ and at least one of $R^{13}$ and $R^{14}$ is selected from the group consisting of alkyl, alkoxy, silyl, and deuterated analogs thereof.

As used herein, "all other sites are H or D" indicates that in the skeletal structure, where H is implied, the compound can have hydrogen or deuterium.

In some embodiments, the diazachrysene derivatives have Formula I(b)

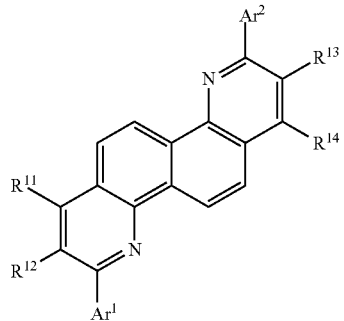

Formula I(b)

wherein:
Ar$^1$ and Ar$^2$ are the same or different and are selected from the group consisting of aryl, aryloxy, and deuterated analogs thereof;
$R^{11}$-$R^{14}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring; and
all other sites are H or D;
with the proviso that at least one of $R^{11}$ and $R^{12}$ and at least one of $R^{13}$ and $R^{14}$ is selected from the group consisting of alkyl, alkoxy, silyl, and deuterated analogs thereof.

In some embodiments, the diazachrysene derivatives have Formula I(c)

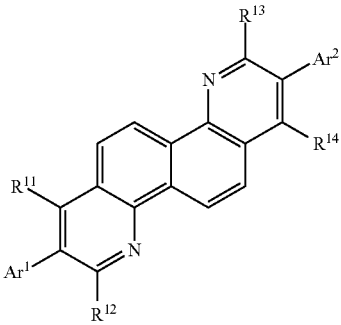

Formula I(c)

wherein:

Ar¹ and Ar² are the same or different and are selected from the group consisting of aryl, aryloxy, and deuterated analogs thereof; $R^{11}$-$R^{14}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring; and all other sites are H or D;

with the proviso that at least one of $R^{11}$ and $R^{12}$ and at least one of $R^{13}$ and $R^{14}$ is selected from the group consisting of alkyl, alkoxy, silyl, and deuterated analogs thereof.

In some embodiments of Formulae I(a) through I(c), Ar¹ and Ar² have Formula a, as defined above.

In some embodiments of Formulae I(a) through I(c), Ar¹ and Ar² have Formula b, as defined above.

In some embodiments of Formulae I(a) through I(c), Ar¹ and Ar² have Formula c, as defined above.

In some embodiments of Formulae I(a) through I(c), Ar¹ and Ar² include a heteroaryl or deuterated heteroaryl group.

In some embodiments of Formulae I(a) through I(c), there are no amino groups.

In some embodiments of Formulae I(a) through I(c), there are no carbazolyl groups.

Some embodiments of Formula I and Formulae I(a) through I(c) also include:

(1) $R^1$ is H or D;
(2) $R^1$ is alkyl or deuterated alkyl;
(3) $R^1$ is alkoxy or deuterated alkoxy;
(4) $R^1$ is silyl or deuterated silyl;
(5) $R^1$ is hydrocarbon aryl or deuterated hydrocarbon aryl;
(6) $R^1$ is heteroaryl or deuterated heteroaryl;
(7) $R^1$ is aryloxy or deuterated aryloxy;
(8) $R^2$ is H or D;
(9) $R^2$ is alkyl or deuterated alkyl;
(10) $R^2$ is alkoxy or deuterated alkoxy;
(11) $R^2$ is silyl or deuterated silyl;
(12) $R^2$ is hydrocarbon aryl or deuterated hydrocarbon aryl;
(13) $R^2$ is heteroaryl or deuterated heteroaryl;
(14) $R^2$ is aryloxy or deuterated aryloxy;
(15) $R^3$ is H or D;
(16) $R^3$ is alkyl or deuterated alkyl;
(17) $R^3$ is alkoxy or deuterated alkoxy;
(18) $R^3$ is silyl or deuterated silyl;
(10) $R^3$ is hydrocarbon aryl or deuterated hydrocarbon aryl;
(20) $R^3$ is heteroaryl or deuterated heteroaryl;
(21) $R^3$ is aryloxy or deuterated aryloxy;
(22) $R^4$ is H or D;
(23) $R^4$ is alkyl or deuterated alkyl;
(24) $R^4$ is alkoxy or deuterated alkoxy;
(25) $R^4$ is silyl or deuterated silyl;
(26) $R^4$ is hydrocarbon aryl or deuterated hydrocarbon aryl;
(27) $R^4$ is heteroaryl or deuterated heteroaryl;
(28) $R^4$ is aryloxy or deuterated aryloxy;
(29) $R^5$ is H or D;
(30) $R^5$ is alkyl or deuterated alkyl;
(31) $R^5$ is alkoxy or deuterated alkoxy;
(32) $R^5$ is silyl or deuterated silyl;
(33) $R^5$ is hydrocarbon aryl or deuterated hydrocarbon aryl;
(34) $R^5$ is heteroaryl or deuterated heteroaryl;
(35) $R^5$ is aryloxy or deuterated aryloxy;
(36) $R^6$ is H or D;
(37) $R^6$ is alkyl or deuterated alkyl;
(38) $R^6$ is alkoxy or deuterated alkoxy;
(39) $R^6$ is silyl or deuterated silyl;
(40) $R^6$ is hydrocarbon aryl or deuterated hydrocarbon aryl;
(41) $R^6$ is heteroaryl or deuterated heteroaryl;
(42) $R^6$ is aryloxy or deuterated aryloxy;
(43) $R^7$ is H or D;
(44) $R^7$ is alkyl or deuterated alkyl;
(45) $R^7$ is alkoxy or deuterated alkoxy;
(46) $R^7$ is silyl or deuterated silyl;
(47) $R^7$ is hydrocarbon aryl or deuterated hydrocarbon aryl;
(48) $R^7$ is heteroaryl or deuterated heteroaryl;
(49) $R^7$ is aryloxy or deuterated aryloxy;
(50) $R^8$ is H or D;
(51) $R^8$ is alkyl or deuterated alkyl;
(52) $R^8$ is alkoxy or deuterated alkoxy;
(53) $R^8$ is silyl or deuterated silyl;
(54) $R^8$ is hydrocarbon aryl or deuterated hydrocarbon aryl;
(55) $R^8$ is heteroaryl or deuterated heteroaryl;
(56) $R^8$ is aryloxy or deuterated aryloxy;
(57) $R^9$ is H or D;
(58) $R^9$ is alkyl or deuterated alkyl;
(59) $R^9$ is alkoxy or deuterated alkoxy;
(60) $R^9$ is silyl or deuterated silyl;
(61) $R^9$ is hydrocarbon aryl or deuterated hydrocarbon aryl;
(62) $R^9$ is heteroaryl or deuterated heteroaryl;
(63) $R^9$ is aryloxy or deuterated aryloxy;
(64) $R^{10}$ is H or D;
(65) $R^{10}$ is alkyl or deuterated alkyl;
(66) $R^{10}$ is alkoxy or deuterated alkoxy;
(67) $R^{10}$ is silyl or deuterated silyl;
(68) $R^{10}$ is hydrocarbon aryl or deuterated hydrocarbon aryl;
(69) $R^{10}$ is heteroaryl or deuterated heteroaryl;
(70) $R^{10}$ is aryloxy or deuterated aryloxy;
(71) $R^1$ and $R^2$ form a ring;
(72) $R^2$ and $R^3$ form a ring;
(73) $R^4$ and $R^5$ form a ring;
(74) $R^5$ and $R^6$ form a ring;
(75) $R^7$ and $R^8$ form a ring;
(76) $R^9$ and $R^{10}$ form a ring;
(77) $R^4$ and $R^5$ forma ring;
(78) $R^5$ and $R^6$ form a ring;
(79) $R^1$=$R^6$;

(80) $R^2=R^5$;
(81) $R^3=R^4$;
(82) $R^7=R^{10}$;
(83) $R^8=R^9$;
(84) $Ar^1$ has Formula a
(85) $Ar^1$ includes a heteroaryl or deuterated heteroaryl group;
(86) $Ar^2$ has Formula a
(87) $Ar^2$ includes a heteroaryl or deuterated heteroaryl group;
(88) $Ar^1=Ar^2$;
(89) $R^{11}$ is H or D;
(90) $R^{11}$ is alkyl or deuterated alkyl;
(91) $R^{11}$ is alkoxy or deuterated alkoxy;
(92) $R^{11}$ is silyl or deuterated silyl;
(93) $R^{11}$ is hydrocarbon aryl or deuterated hydrocarbon aryl;
(94) $R^{11}$ is heteroaryl or deuterated heteroaryl;
(95) $R^{11}$ is aryloxy or deuterated aryloxy;
(96) $R^{12}$ is H or D;
(97) $R^{12}$ is alkyl or deuterated alkyl;
(98) $R^{12}$ is alkoxy or deuterated alkoxy;
(99) $R^{12}$ is silyl or deuterated silyl;
(100) $R^{12}$ is hydrocarbon aryl or deuterated hydrocarbon aryl;
(101) $R^{12}$ is heteroaryl or deuterated heteroaryl;
(102) $R^{12}$ is aryloxy or deuterated aryloxy;
(103) $R^{13}$ is H or D;
(104) $R^{13}$ is alkyl or deuterated alkyl;
(105) $R^{13}$ is alkoxy or deuterated alkoxy;
(106) $R^{13}$ is silyl or deuterated silyl;
(107) $R^{13}$ is hydrocarbon aryl or deuterated hydrocarbon aryl;
(108) $R^{13}$ is heteroaryl or deuterated heteroaryl;
(109) $R^{13}$ is aryloxy or deuterated aryloxy;
(110) $R^{14}$ is H or D;
(111) $R^{14}$ is alkyl or deuterated alkyl;
(112) $R^{14}$ is alkoxy or deuterated alkoxy;
(113) $R^{14}$ is silyl or deuterated silyl;
(114) $R^{14}$ is hydrocarbon aryl or deuterated hydrocarbon aryl;
(115) $R^{14}$ is heteroaryl or deuterated heteroaryl;
(116) $R^{14}$ is aryloxy or deuterated aryloxy;
(117) $R^{11}$ and $R^{12}$ form a ring;
(118) $R^{13}$ and $R^{14}$ form a ring;
(110) $R^4$ and $R^5$ forma ring;
(120) $R^5$ and $R^6$ form a ring;
(121) $R^{11}=R^{14}$;
(122) $R^{12}=R^{13}$.

Any of the above specific and/or general embodiments can be combined with one or more of the other embodiments, so long as they are not mutually exclusive. For example, the embodiment in which at least one of $R^1$-$R^3$ is a heteroaryl or deuterated heteroaryl group can be combined with the embodiment in which $R^4$ a silyl or deuterated silyl. The same is true for the other non-mutually-exclusive embodiments discussed above. The skilled person would understand which embodiments were mutually exclusive and would thus readily be able to determine the combinations of embodiments that are contemplated by the present application.

Some examples of compounds having Formula I are shown below.

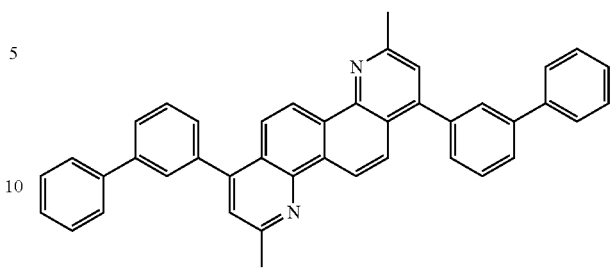

Compound 1

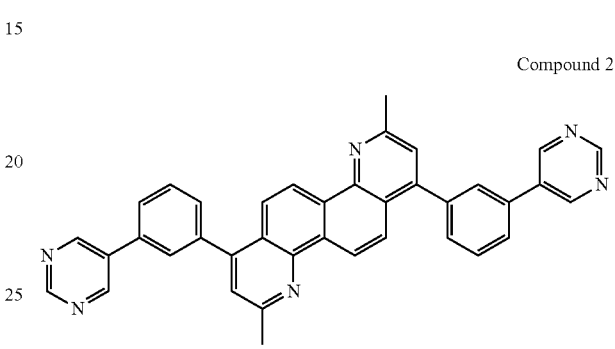

Compound 2

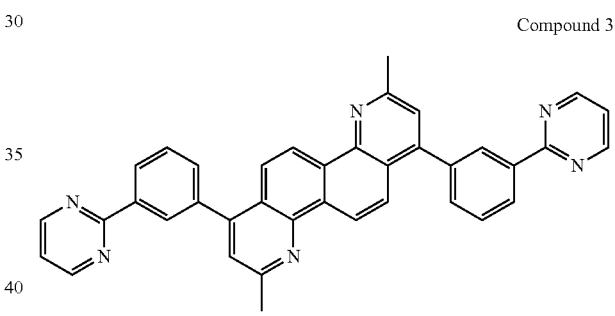

Compound 3

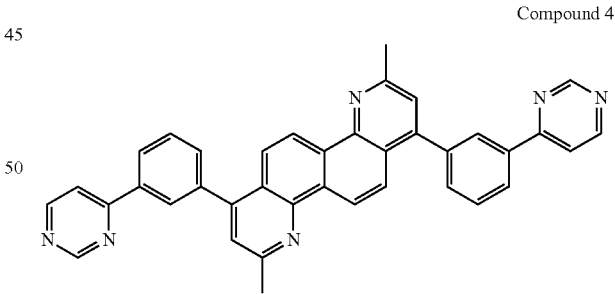

Compound 4

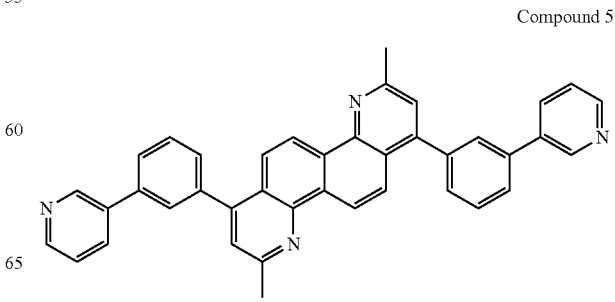

Compound 5

-continued
Compound 6
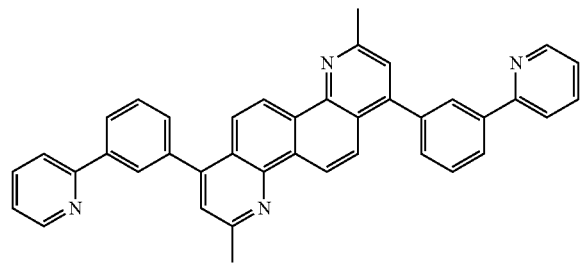
Compound 7
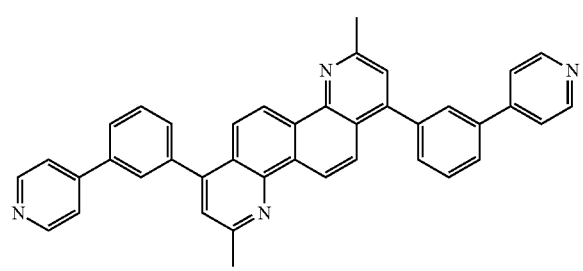
Compound 8
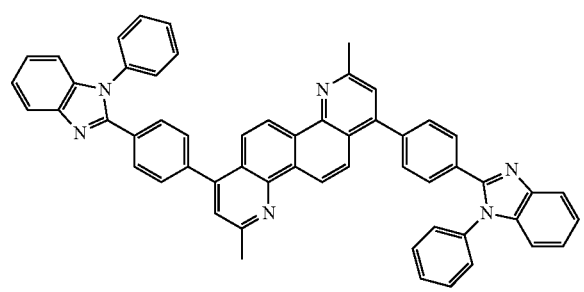
Compound 9
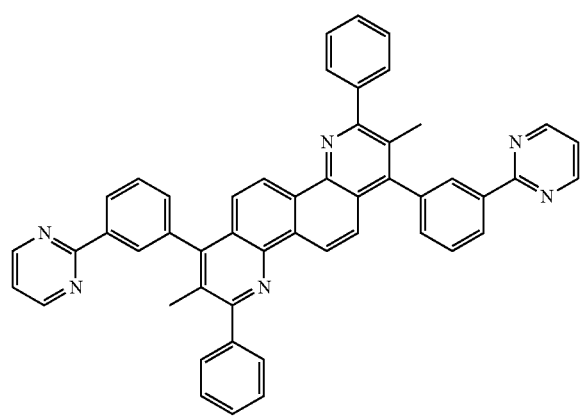
Compound 10
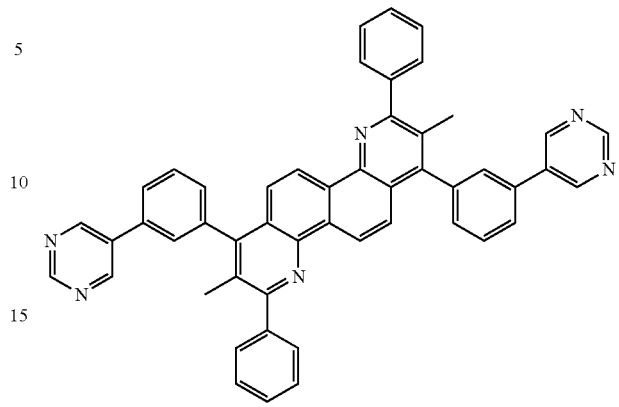
Compound 11
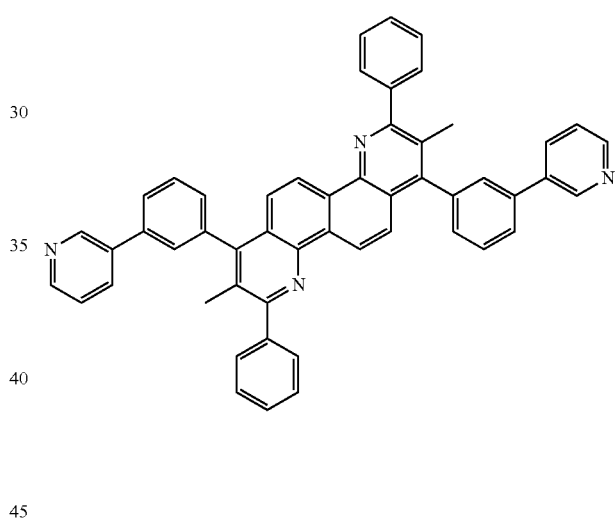
Compound 12
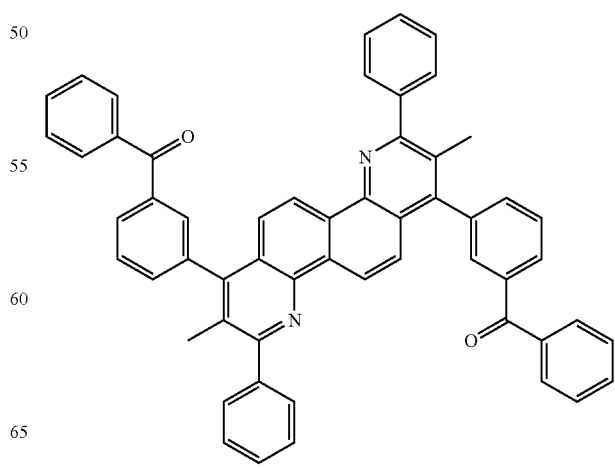

Compound 13
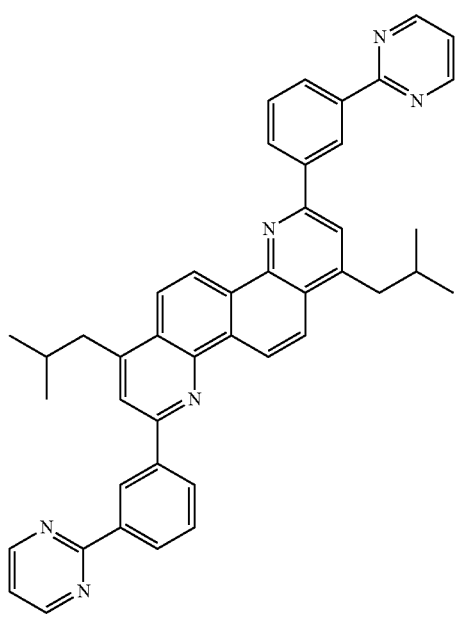
Compound 14
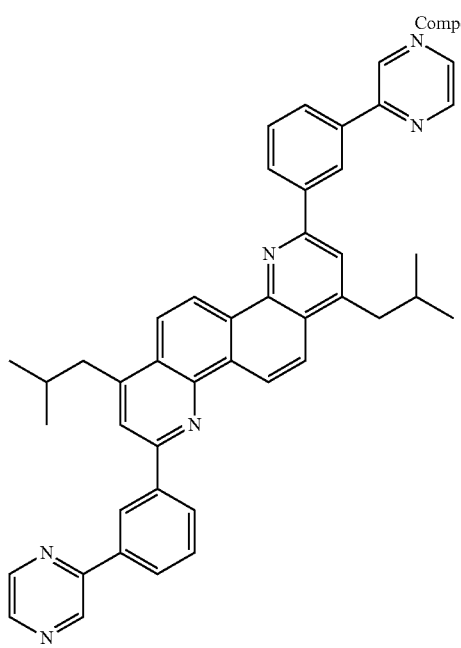
Compound 15
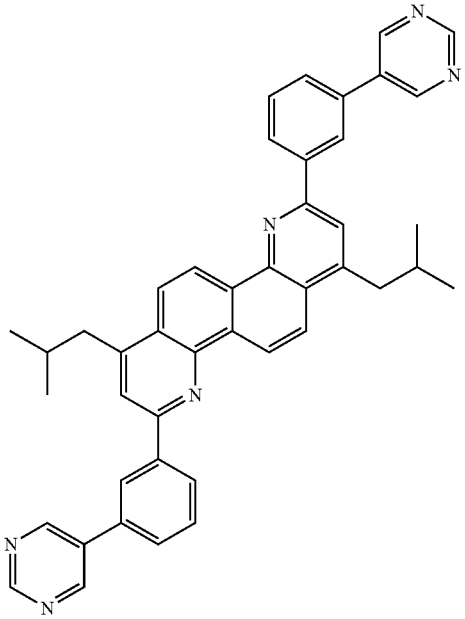
Compound 16
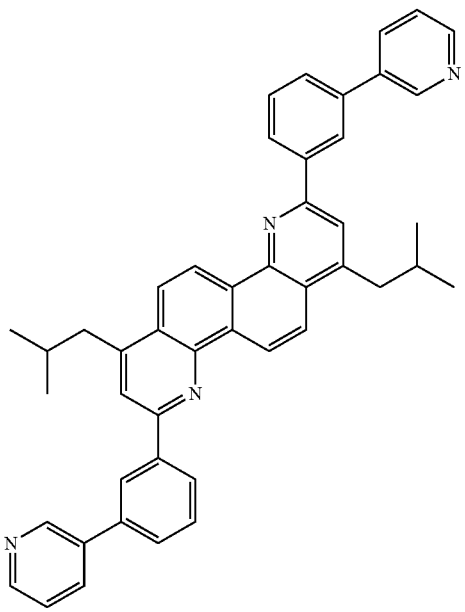

Compound 17
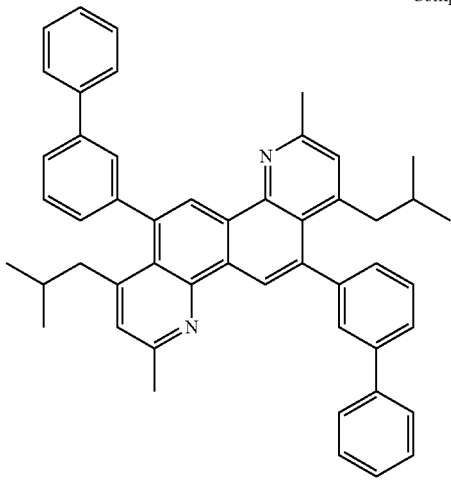
Compound 20
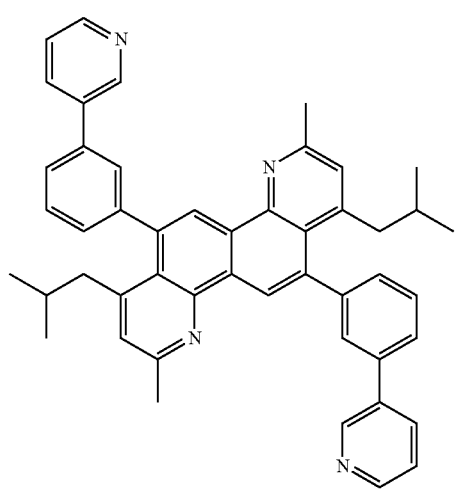
Compound 18
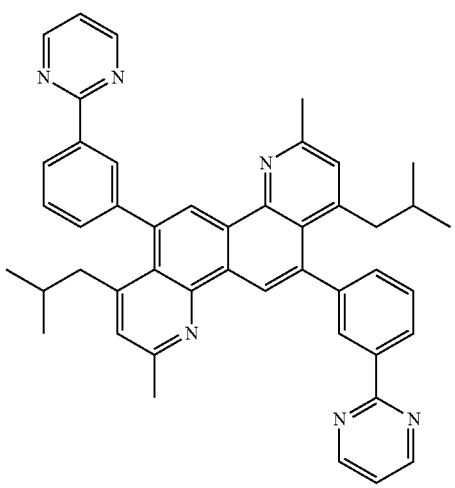
Compound 21
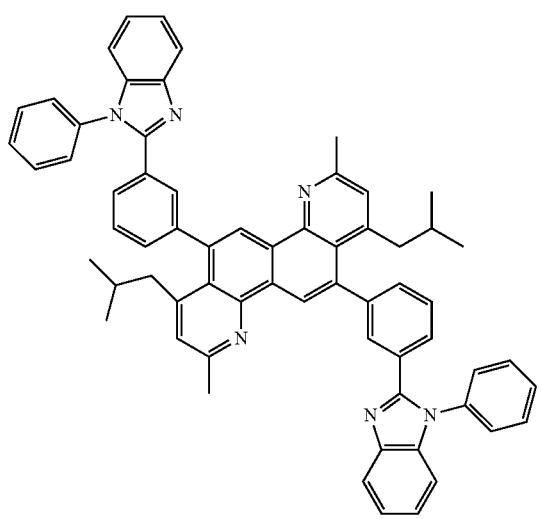
Compound 19
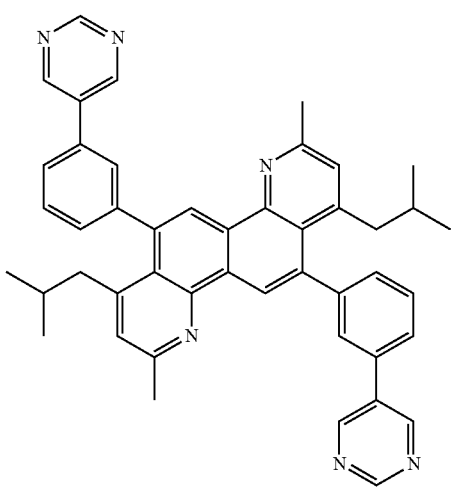
Compound 22
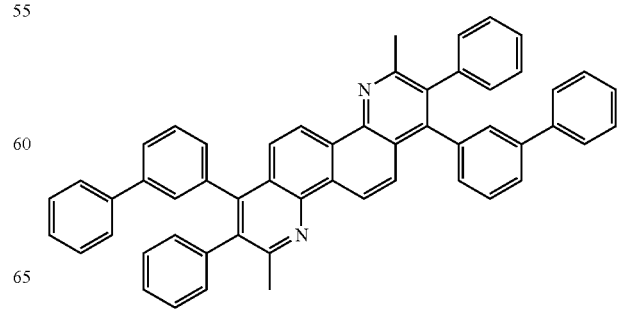

Compound 23
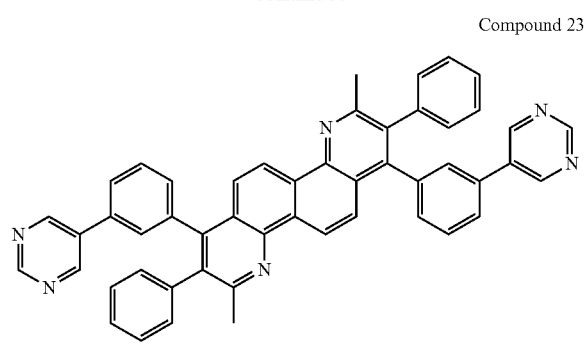
Compound 28
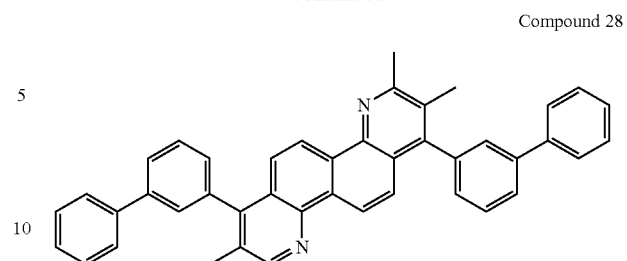
Compound 24
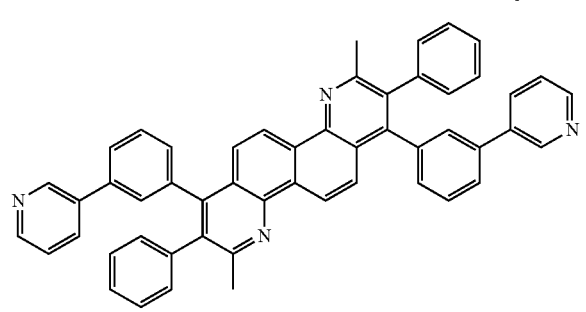
Compound 29
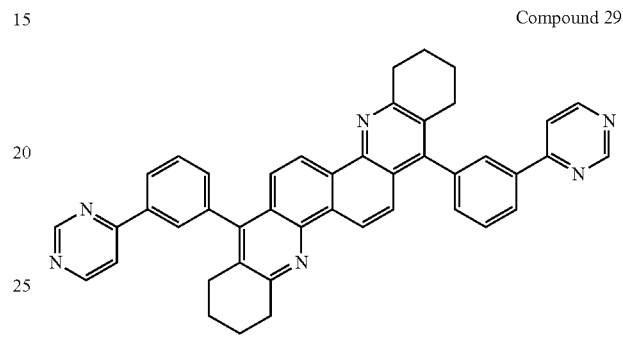
Compound 25
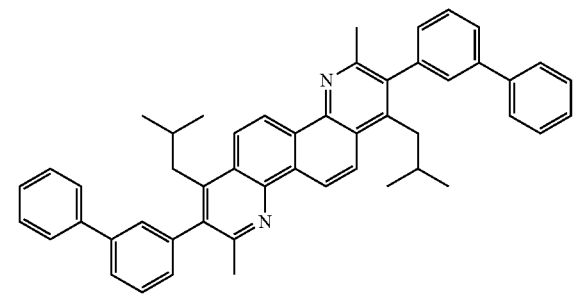
Compound 30
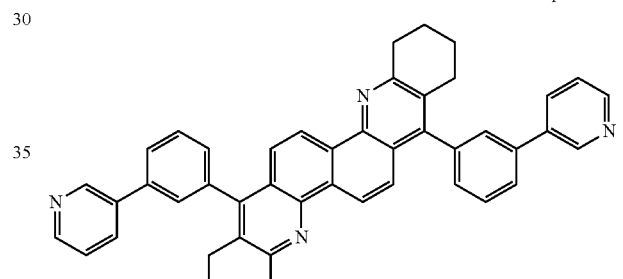
Compound 26
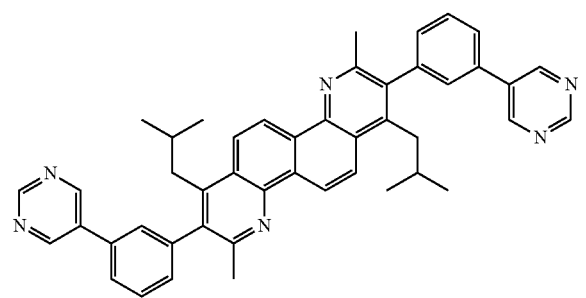
Compound 31
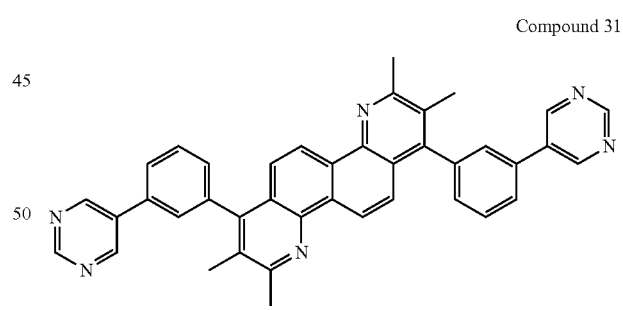
Compound 27
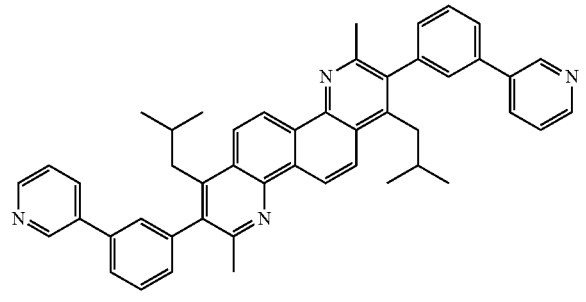
Compound 32
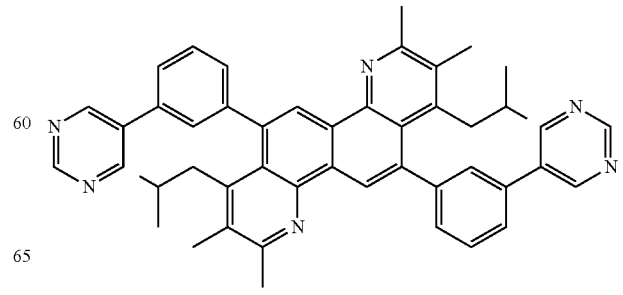

Compound 33

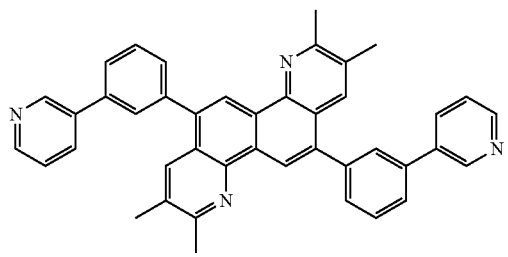

Compound 34

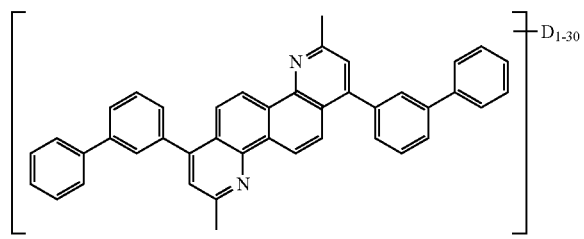

Compound 35

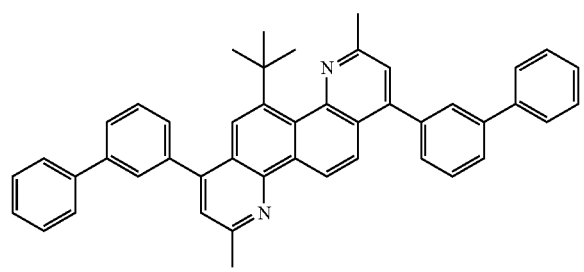

Compound 36

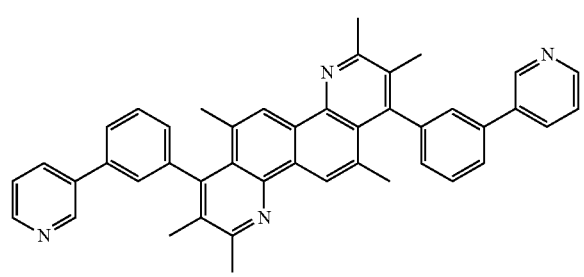

Compound 37

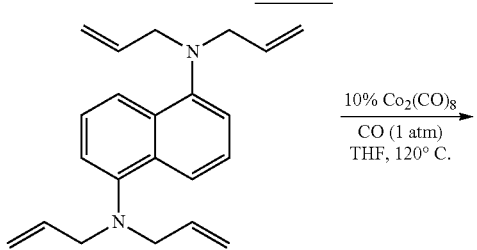

Compound 38

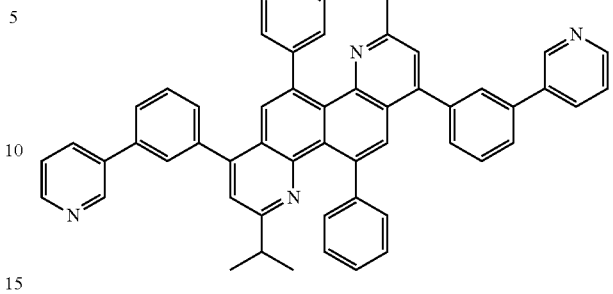

Compound 39

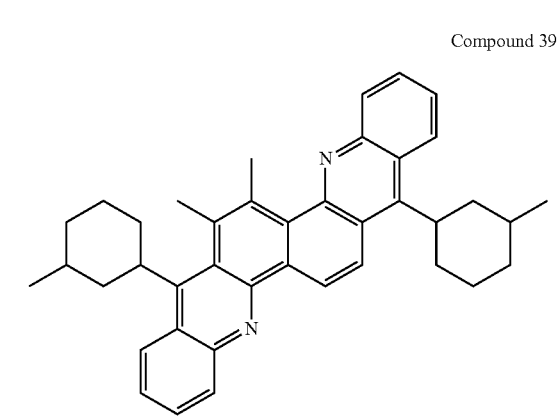

The diazachrysene compounds having Formula I can be made by known synthetic techniques. Several well-known methods used for the synthesis of quinolines can be used for the preparation of diazachrysene compounds. A review of quinoline syntheses can be found in the book "Contemporary Heterocyclic Chemistry" by G. R. Newkome and W. W. Paudler (New York: John Wiley & Sons, 1082; Chapter 15.1.2 therein). The synthesis of 4,10-diazachrysenes has been accomplished most commonly by ring annulation of 1,5-diaminonaphthalene. For example, the compounds can be prepared by cobalt-carbonyl catalyzed bis-cyclization of N1,N1,N5,N5-tetraallylnaphthalene-1,5-diamine as described in *J. Org. Chem.* 2003, 68, 3563-8 and depicted in Scheme 1.

Scheme 1.

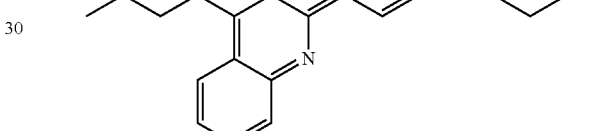

-continued

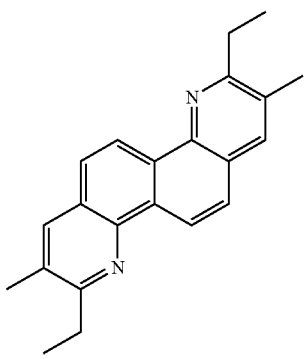

Another method by which 4,10-diazachrysenes have been prepared is via cyclization of α-oxoketene-N,S-anilinoacetals with the Vilsmeier-Haack reagent. This method was applied to naphthalene-1,5-diamine as depicted in Scheme 2 and described in *J. Org. Chem.* 2003, 68, 3966-75.

Scheme 2

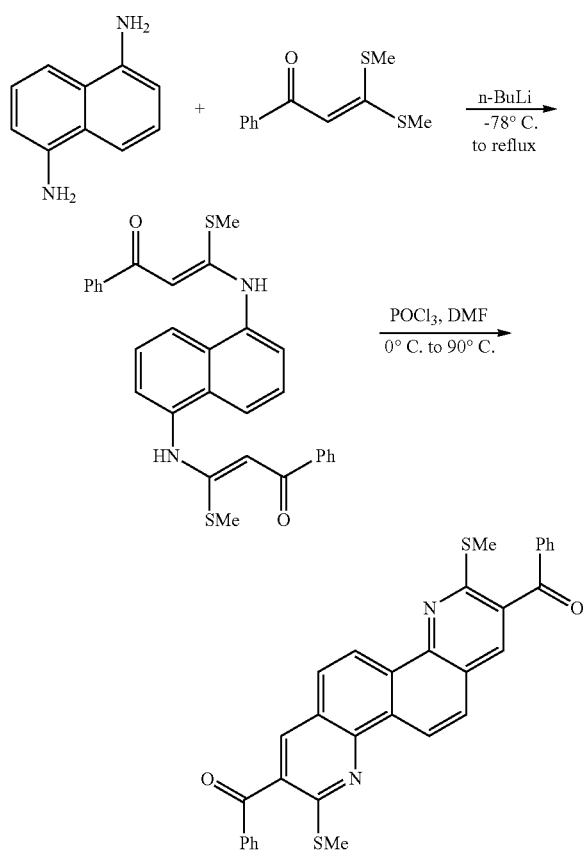

4,10-Diazachrysenes having substituents in the 1,7-position, as in the case of some of the examples described herein, have been prepared via Conrad-Limpach cyclization of the bis(enamine) derived from addition of naphthalene-1,5-diamine to dimethylacetylene dicarboxylate using Eaton's reagent. This is illustrated by the example from *J. Org. Chem.* 2007, 72, 4276-9, shown in Scheme 3. The resulting bis-quinolones can then be converted to the 1,7-dichloro-4, 10-diazachysenes by treatment with phosphorus oxychloride as described in the published PCT application, WO2012-082593.

Scheme 3

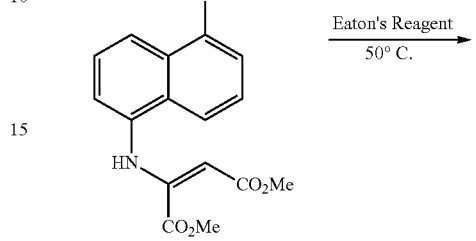

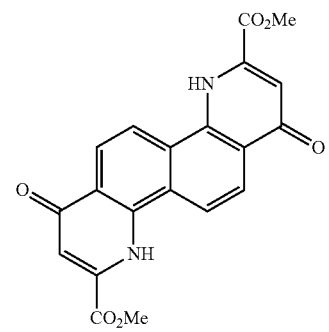

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCI, etc. Deuteration reactions have also been described in published PCT application WO2011-053334.

3. ELECTROACTIVE COMPOSITION

There is also provided a composition comprising (a) a host compound having Formula I and (b) a dopant capable of electroluminescence having an emission maximum between 380 and 750 nm. The diazachrysene derivatives of Formula I are useful as host materials for photoactive materials. The compounds can be used alone, or in combination with another host material. The compounds of Formula I can be used as a host for dopants with any color of emission. In some embodiments, the compound as used as hosts for organometallic electroluminescent material.

In some embodiments, the composition comprises (a) a host compound having Formula I and (b) a photoactive dopant capable of electroluminescence having an emission maximum between 380 and 750 nm. In some embodiments, the composition consists essentially of (a) a host compound having Formula I and (b) a photoactive dopant capable of electroluminescence having an emission maximum between 380 and 750 nm. In some embodiments, the composition comprises (a) a host compound having Formula I, (b) a photoactive dopant capable of electroluminescence having an emission maximum between 380 and 750 nm, and (c) a second host material. In some embodiments, the composition comprises (a) a host compound having Formula I, (b) a photoactive dopant capable of electroluminescence having an emission maximum between 380 and 750 nm, and (c) a second host material.

The amount of dopant present in the composition is generally in the range of 3-20% by weight, based on the total weight of the composition; in some embodiments, 5-15% by weight. When a second host is present, the ratio of first host having Formula I to second host is generally in the range of 1:20 to 20:1; in some embodiments, 5:15 to 15:5. In some embodiments, the first host material having Formula I is at least 50% by weight of the total host material; in some embodiments, at least 70% by weight.

Electroluminescent ("EL") materials which can be used as a dopant include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds and cyclometallated complexes of metals such as iridium and platinum. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red light-emitting materials include, but are not limited to, complexes of Ir having phenylquinoline or phenylisoquinoline ligands, periflanthenes, diazachrysenes, and perylenes. Red light-emitting materials have been disclosed in, for example, U.S. Pat. No. 6,875,524, and published US application 2005-0158577.

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published PCT application WO 2007/021117.

Examples of blue light-emitting materials include, but are not limited to, complexes of Ir having phenylpyridine or phenylimidazole ligands, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

In some embodiments, the dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral and is a tris-cyclometallated complex of iridium having the formula $IrL_3$ or a bis-cyclometallated complex of iridium having the formula $IrL_2Y$. In some embodiments, L is a monoanionic bidentate cyclometalating ligand coordinated through a carbon atom and a nitrogen atom. In some embodiments, L is an aryl N-heterocycle, where the aryl is phenyl or napthyl, and the N-heterocycle is pyridine, quinoline, isoquinoline, diazine, pyrrole, pyrazole or imidazole. In some embodiments, Y is a monoanionic bidentate ligand. In some embodiments, L is a phenylpyridine, a phenylquinoline, or a phenylisoquinoline. In some embodiments, Y is a β-dienolate, a diketimine, a picolinate, or an N-alkoxypyrazole. The ligands may be unsubstituted or substituted with F, D, alkyl, perfluororalkyl, alkoxyl, alkylamino, arylamino, CN, silyl, fluoroalkoxyl or aryl groups.

In some embodiments, the dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the dopant is a complex having the formula $Ir(L1)_a(L2)_b(L3)_c$; where
   L1 is a monoanionic bidentate cyclometalating ligand coordinated through carbon and nitrogen;
   L2 is a monoanionic bidentate ligand which is not coordinated through a carbon;
   L3 is a monodentate ligand;
   a is 1-3;
   b and c are independently 0-2; and
   a, b, and c are selected such that the iridium is hexacoordinate and the complex is electrically neutral.

Some examples of formulae include, but are not limited to, $Ir(L1)_3$; $Ir(L1)_2(L2)$; and $Ir(L1)_2(L3)(L3')$, where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

Monodentate ligand L3 can be anionic or nonionic. Anionic ligands include, but are not limited to, H⁻ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls. The iridium complex dopants can be made using standard synthetic techniques as described in, for example, U.S. Pat. No. 6,670,645.

In some embodiments, the dopant is a small organic luminescent compound. In some embodiments, the dopant is selected from the group consisting of a non-polymeric spirobifluorene compound and a diazachrysene compound.

In some embodiments, the dopant is a compound having aryl amine groups. In some embodiments, the photoactive dopant is selected from the formulae below:

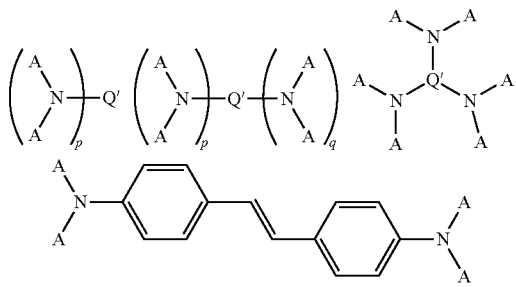

where:

A is the same or different at each occurrence and is an aromatic group having from 3-60 carbon atoms;

Q' is a single bond or an aromatic group having from 3-60 carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

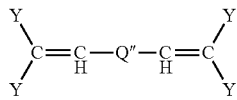

where:

Y is the same or different at each occurrence and is an aromatic group having 3-60 carbon atoms;

Q'' is an aromatic group, a divalent triphenylamine residue group, or a single bond.

In some embodiments, the dopant is an aryl acene. In some embodiments, the dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the diazachrysene derivative compound is used with an additional host material. In some embodiments, the diazachrysene derivative compound is not used as a host in the photoactive layer. Examples of other types of hosts which can be used alone or in combination with the diazachrysene derivative compounds, include, but are not limited to, indolocarbazoles, chrysenes, phenanthrenes, triphenylenes, phenanthrolines, triazines, naphthalenes, anthracenes, quinolines, isoquinolines, quinoxalines, phenylpyridines, benzodifurans, and metal quinolinate complexes, and deuterated analogs thereof.

4. ORGANIC ELECTRONIC DEVICE

Organic electronic devices that may benefit from having one or more layers comprising the deuterated materials described herein include, but are not limited to, (1) devices that convert electrical energy into radiation (e.g., a light-emitting diode, light-emitting diode display, light-emitting luminaire, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a thin film transistor or diode). The compounds of the invention often can be useful in applications such as oxygen sensitive indicators and as luminescent indicators in bioassays.

In some embodiments, an organic electronic device comprises at least one layer comprising the compound having Formula I as discussed above.

In some embodiments, the electronic device comprises at least one electroactive layer positioned between two electrical contact layers, wherein the at least one electroactive layer of the device includes a diazachrysene derivative compound having Formula I.

An example of an organic electronic device structure is shown in FIG. 1. The device 100 has a first electrical contact layer, an anode layer 110 and a second electrical contact layer, a cathode layer 160, and a photoactive layer 140 between them. Adjacent to the anode may be a hole injection layer 120. Adjacent to the hole injection layer may be a hole transport layer 130, comprising hole transport material. Adjacent to the cathode may be an electron transport layer 150, comprising an electron transport material. Devices may use one or more additional hole injection or hole transport layers (not shown) next to the anode 120 and/or one or more additional electron injection or electron transport layers (not shown) next to the cathode 160.

Layers 120 through 150 are individually and collectively referred to as the electroactive layers.

In some embodiments, the photoactive layer 140 is pixelated, as shown in FIG. 2. Layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, In some embodiments 1000-2000 Å; hole injection layer 120, 50-2000 Å, In some embodiments 200-1000 Å; hole transport layer 130, 50-2000 Å, In some embodiments 200-1000 Å; photoactive layer 140, 10-2000 Å, In some embodiments 100-1000 Å; electron transport layer 150, 50-2000 Å, In some embodiments 100-1000 Å; cathode 160, 200-10000 Å, In some embodiments 300-5000 Å. The location of the electron-hole recombination zone in the device, and thus the emission spectrum of the device, can be affected by the relative thickness of each layer. The desired ratio of layer thicknesses will depend on the exact nature of the materials used. In some embodiments, the devices have additional layers to aid in processing or to improve functionality.

Depending upon the application of the device 100, the photoactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1066). Devices with light-emitting layers may be used to form displays or for lighting applications, such as white light luminaires.

One or more of the new diazachrysene compounds described herein may be present in one or more of the electroactive layers of a device.

In some embodiments, the new diazachrysene compounds having Formula I are useful as host materials for photoactive dopant materials in photoactive layer 140. It has been found that when these compounds are used by themselves or in conjunction with other cohosts, they can provide improved efficiency and lifetime in OLED devices. It has been discovered through calculations that these compounds have high triplet energies and HOMO and LUMO levels appropriate for charge transport, making them excellent host materials for organometallic emitters.

In some embodiments, the new electroactive compounds are useful as electron transport materials in layer 150.

Photoactive Layer

In some embodiments, the photoactive layer 140 comprises the electroactive composition described above.

In some embodiments, the dopant is an organometallic material. In some embodiments, the organometallic material is a complex of Ir or Pt. In some embodiments, the organometallic material is a cyclometallated complex of Ir.

In some embodiments, the photoactive layer comprises (a) a host material having Formula I and (b) one or more dopants. In some embodiments, the photoactive layer comprises (a) a host material having Formula I and (b) an organometallic electroluminescent dopant. In some embodiments, the photoactive layer comprises (a) a host material having Formula I, (b) a photoactive dopant, and (c) a second host material. In some embodiments, the photoactive layer comprises (a) a host material having Formula I, (b) an organometallic complex of Ir or Pt, and (c) a second host material. In some embodiments, the photoactive layer comprises (a) a host material having Formula I, (b) a cyclometallated complex of Ir, and (c) a second host material.

In some embodiments, the photoactive layer consists essentially of (a) a host material having Formula I and (b) one or more dopants. In some embodiments, the photoactive layer consists essentially of (a) a host material having Formula I and (b) an organometallic electroluminescent dopant. In some embodiments, the photoactive layer consists essentially of (a) a host material having Formula I, (b) a photoactive dopant, and (c) a second host material. In some embodiments, the photoactive layer consists essentially of (a) a host material having Formula I, (b) an organometallic complex of Ir or Pt, and (c) a second host material. In some embodiments, the photoactive layer consists essentially of (a) a host material having Formula I, (b) a cyclometallated complex of Ir, and (c) a second host material.

In some embodiments, the photoactive layer consists essentially of (a) a host material having Formula I, wherein the compound is deuterated, and (b) one or more dopants. In some embodiments, the photoactive layer consists essentially of a host material having Formula I, wherein the compound is deuterated, and (b) an organometallic electroluminescent dopant. In some embodiments, the photoactive layer consists essentially of (a) a host material having Formula I, wherein the compound is deuterated, (b) a photoactive dopant, and (c) a second host material. In some embodiments, the photoactive layer consists essentially of a host material having Formula I, wherein the compound is deuterated, (b) an organometallic complex of Ir or Pt, and (c) a second host material. In some embodiments, the photoactive layer consists essentially of (a) a host material having Formula I, wherein the compound is deuterated a host material having Formula I, wherein the compound is deuterated, (b) a cyclometallated complex of Ir, and (c) a second host material. In some embodiments, the deuterated compound of Formula I is at least 10% deuterated; in some embodiments, at least 50% deuterated. In some embodiments, the second host material is deuterated. In some embodiments, the second host material is at least 10% deuterated; in some embodiments, at least 50% deuterated.

Electron Transport Layer

The diazachrysene derivative compounds of Formula I are useful as electron transport materials in layer 150. The compounds can be used alone, or in combination with another electron transport material. In some embodiments, the electron transport layer consists essentially of a diazachrysene derivative compound of Formula I.

Examples of other electron transport materials which can be used alone or in combination with the diazachrysene derivative compounds include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1092). At least one of the anode and cathode is desirably at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. In some embodiments, the hole injection layer comprises an electrically conductive polymer doped with a fluorinated acid polymer. materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1096, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and $Li_2O$ can also be deposited between the organic layer and the cathode layer to lower the operating voltage.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, electroactive layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

In some embodiments, the device is fabricated by liquid deposition of the buffer layer, the hole transport layer, and the photoactive layer, and by vapor deposition of the anode, the electron transport layer, an electron injection layer and the cathode.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials may also be considerations in selecting the electron and hole transport materials.

It is understood that the efficiency of devices made with the diazachrysene derivative compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The concepts described herein will be further described in the following examples, which do not limit the scope of the invention described in the claims.

Synthesis Example 1

This example illustrates the synthesis of Compound 1,3,9-dimethyl-1,7-bis(3-phenylphenyl)-4,10-diazachrysene.

Step 1:

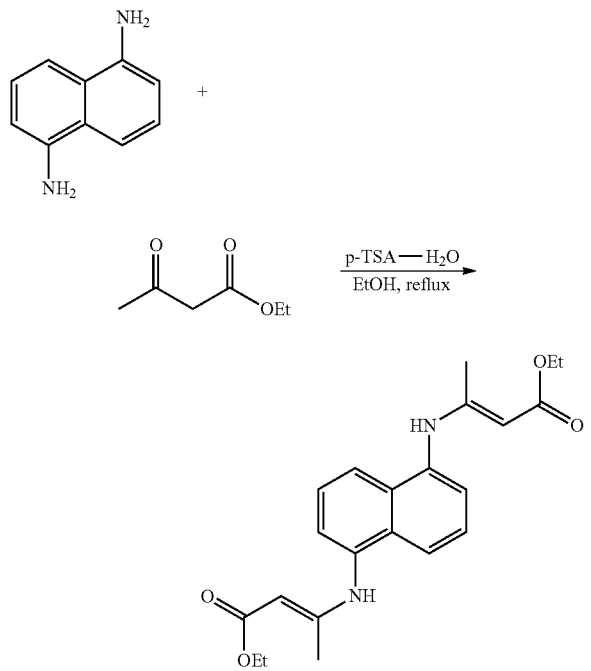

A 3-neck 1 L round bottomed flask equipped with magnetic stir bar, side arm stoppers, nitrogen inlet, reflux condenser and Dean-Stark apparatus containing 4 Å molecular sieves was charged with naphthalene-1,5-diamine (11.1 g, 70 mmol), ethyl acetoacetate (91.1 g, 700 mmol) and absolute ethanol (500 mL) and the mixture was sparged with nitrogen for 15 minutes, then p-toluenesulfonic acid monohydrate (6.7 g, 35 mmol) was added and the mixture was heated under reflux for 18 h. The reaction mixture was cooled to room temperature and the volatiles were removed by rotary evaporation to give a light brown solid that was triturated with hot isopropanol (500 mL), filtered and rinsed with room temperature isopropanol (150 mL) to provide ethyl 3-[[5-[3-ethoxy-1-methyl-3-oxo-prop-1-enyl]amino]-1-naphthyl]amino]but-2-enoate (22.1 g, 83% yield) as an off-white solid.

Step 2:

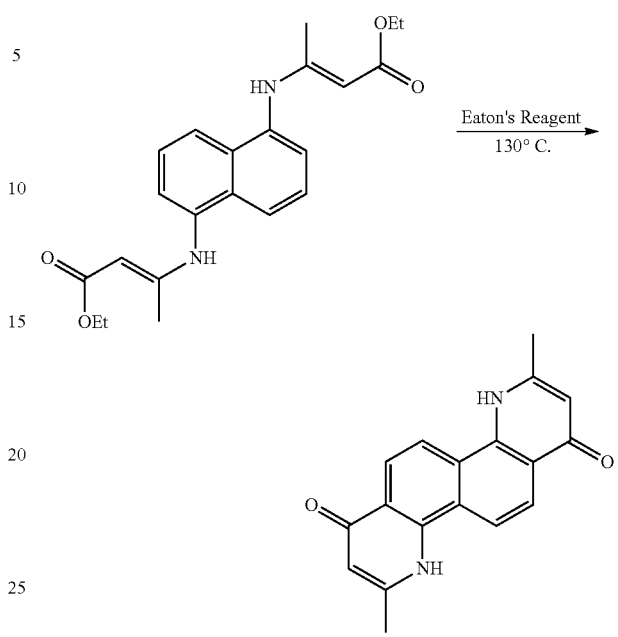

A mixture of ethyl 3-[[5-[3-ethoxy-1-methyl-3-oxo-prop-1-enyl]amino]-1-naphthyl]amino]but-2-enoate (22.1 g, 57.8 mmol) from the previous step and Eaton's reagent (66 mL) was heated at 130° C. for 18 h, cooled to room temperature and cautiously poured into excess aqueous sodium carbonate with vigorous stirring (Caution: gas evolution). The precipitate was collected by vacuum filtration. The wet solid was suspended in toluene (200 mL) and concentrated by rotary evaporation to remove residual water. Further drying under high vacuum gave 1,7-dihydroxy-3,9-dimethyl-4,10-diazachrysene (16.7 g, crude) as a light-brown solid, the structure of which was confirmed by $^1$H NMR spectroscopy of a sample dissolved in trifluoroacetic acid-d.

Step 3:

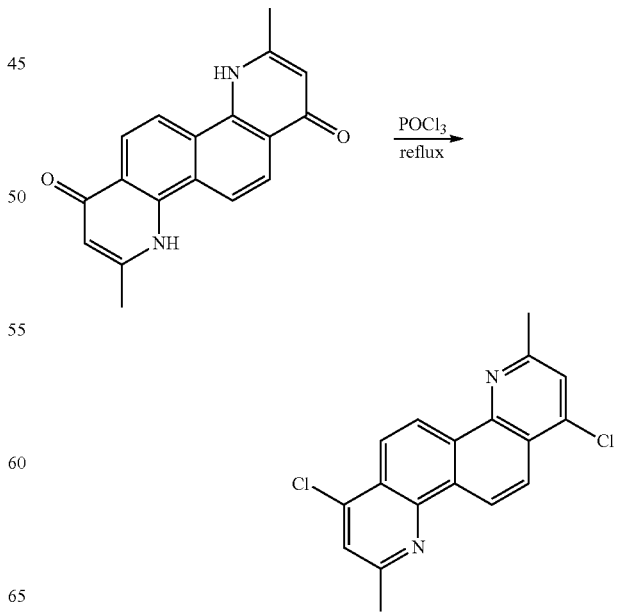

The crude 1,7-dihydroxy-3,9-dimethyl-4,10-diazachrysene (16.7 g, 57.5 mmol, theoretical) from the previous step was suspended in phosphorus oxychloride (158 mL, 1.73 mol) and heated at reflux for 18 h, then cooled to room temperature and cautiously poured into ice water with vigorous stirring. After basification of the aqueous mixture to pH 9 by careful addition of sodium carbonate (Caution: gas evolution) the resulting precipitate was collected by vacuum filtration and washed with water and isopropanol (100 mL each). After drying under high vacuum, the crude brown solid was purified by continuous extraction with refluxing toluene through a 3 cm (diameter)×9 cm (height) extraction thimble charged with a plug of silica gel (30 g) in a modified soxhlet extraction apparatus having a frit bottom in the extraction chamber. After 2 days of continuous extraction the toluene extract was cooled to room temperature and the precipitated light-orange solid was collected by filtration. The solid was then triturated with hot 3/1 toluene/1,4-dioxane (400 mL) and gravity filtered, rinsing with hexanes and isopropanol (30 mL each) to give 1,7-dichloro-3,9-dimethyl-4,10-diazachrysene (9.8 g, 52% yield over two steps) as an off-white solid having 99.1% purity by UPLC. The structure was confirmed by $^1$H NMR spectroscopy of a sample dissolved in trifluoroacetic acid-d.

Step 4:

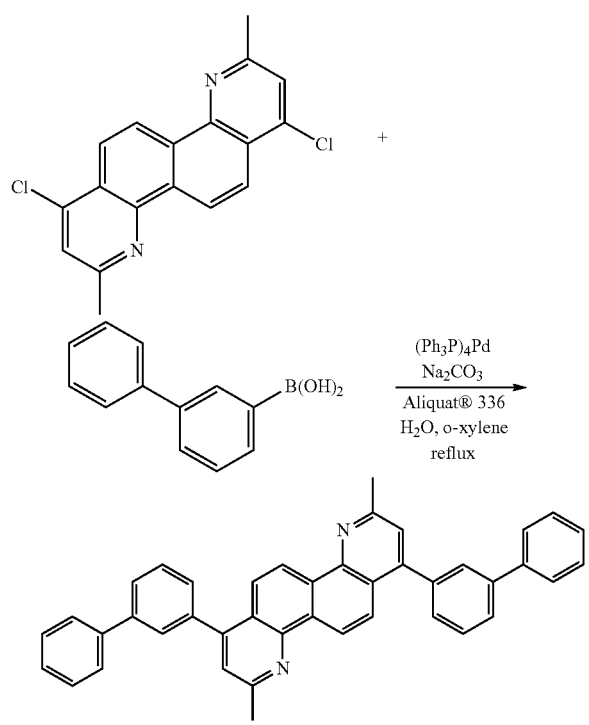

A mixture of 1,7-dichloro-3,9-dimethyl-4,10-diazachrysene (1.96 g, 6.00 mmol) from the previous step, 3-biphenylboronic acid (2.85 g, 14.4 mmol), 2.0 M aqueous sodium carbonate (37.5 mL) and Aliquat® 336 (485 mg, 1.20 mmol) in o-xylene (75 mL) was sparged with nitrogen for 30 minutes and tetrakis(triphenylphosphine)palladium(0) (347 mg, 0.30 mmol) was added and the mixture was heated at reflux for 18 h. After cooling to room temperature the bi-layer reaction mixture was separated in a separatory funnel. The aqueous layer was extracted with ethyl acetate (3×50 mL). The combined organic layer was washed with brine (2×150 mL), dried over magnesium sulfate, filtered and concentrated. The crude brown solid was crystallized by dissolving a minimum amount of toluene (approximately 200 mL) in a 90° C. hot water bath. To the saturated solution was added an equal volume of hexane. The saturated solution was cooled to room temperature overnight. The precipitate formed was collected via gravity filtration to give, after washing with isopropanol (50 mL), a first crop of white powdery solid. A second crop was obtained by concentrating the collected filtrate, and repeating the crystallization procedure as described above. The two crops were combined and recrystallized twice more in the same way and then triturated with hot isopropanol (300 mL) to give a solid having approximately 99% by UPLC. Further purification by silica gel MPLC (0-100% dichloromethane in hexanes and another recrystallization from toluene/hexanes as described above, gave 3,9-dimethyl-1,7-bis(3-phenylphenyl)-4,10-diazachrysene (1.22 g, 36% yield) as a white solid with 99.7% purity by UPLC. The structure was confirmed by $^1$H NMR spectroscopy of a sample dissolved in trifluoroacetic acid-d. The product was subjected to vapor sublimation as a final purification step.

Synthesis Example 2

This example illustrates the synthesis of Compound 3, 3,9-dimethyl-1,7-bis(3-pyrimidin-2-ylphenyl)-4,10-diazachrysene.

Step 1:

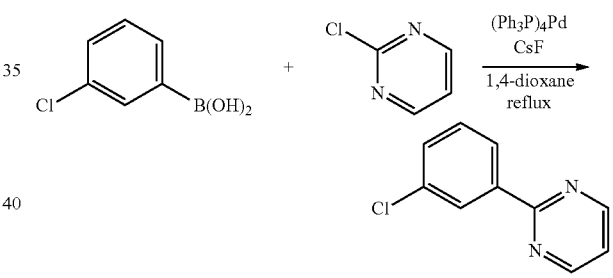

A mixture of 3-chlorophenyl boronic acid (12.04 g, 77.0 mmol), 2-chloropyrimidine (8.02 g, 70.0 mmol), cesium fluoride (23.39 g, 154.0 mmol) and tetrakis(triphenylphosphine)palladium(0) (2.43 g, 2.10 mmol) in 1,4-dioxane (233 mL) was heated at reflux for 17 h, cooled to room temperature, diluted with water (250 mL) and extracted with diethyl ether three times. The combined organic layer was dried over magnesium sulfate, filtered and concentrated to a crude red oil that was pre-adsorbed onto silica gel and purified by silica gel MPLC (0-100% ethyl acetate in hexanes). Pure fractions eluting in 8-12% ethyl acetate in hexanes were combined and concentrated to give 2-(3-chlorophenyl)pyrimidine (4.90 g, 37% yield) as a white solid.

Step 2:

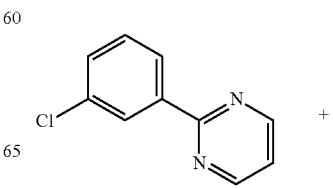

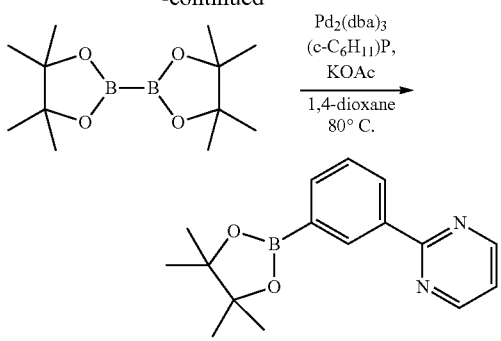

In a glovebox, tricyclohexylphosphine (673 mg, 2.40 mmol) and tris(dibenzylidineacetone)dipalladium(0) (274 mg, 0.30 mmol) were added to a mixture of 2-(3-chlorophenyl)pyrimidine (1.90 g, 10.0 mmol) from the previous step, bis(pinacolato)diboron (3.05 g, 12.0 mmol) and potassium acetate (2.94 g, 30.0 mmol) in 1,4-dioxane (50 mL). The mixture was heated at 80° C. (internal temperature) for 72 h. Additional tricyclohexylphosphine (673 mg, 2.40 mmol) and tris(dibenzylidineacetone)dipalladium(0) (274 mg, 0.30 mmol) were added and heating was resumed for another 18 h. The reaction mixture was cooled to room temperature and filtered and rinsed with dichloromethane. The filtrate was concentrated to a brown oil that was pre-adsorbed onto silica gel and purified by silica gel MPLC (0-100% ethyl acetate in hexanes). Pure fractions eluting in 15-20% ethyl acetate in hexanes were combined and concentrated to give 2-[3-(4,4,5,5-tetramethyl-1,3,2-dioxaborolan-2-yl)phenyl]pyrimidine (1.95 g, 69% yield) as a white solid.

Step 3:

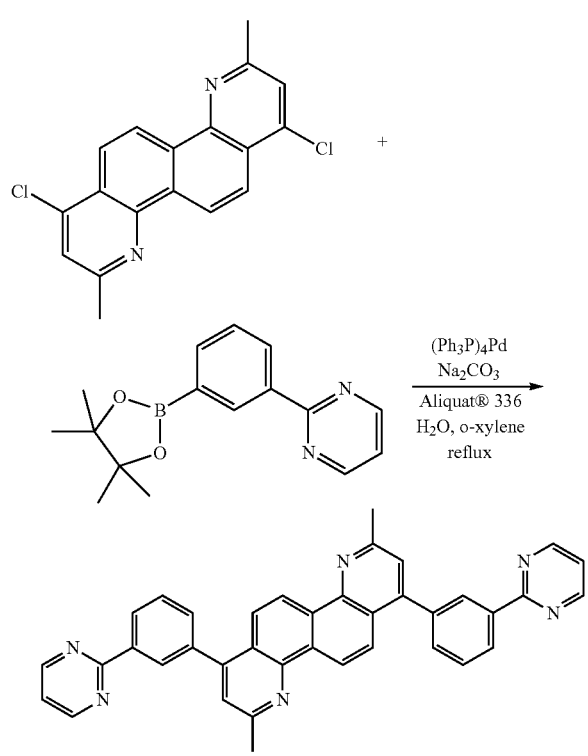

A mixture of 1,7-dichloro-3,9-dimethyl-4,10-diazachrysene (2.94 g, 9.00 mmol) from the Step 3 of Synthesis Example 1, 2-[3-(4,4,5,5-tetramethyl-1,3,2-dioxaborolan-2-yl)phenyl]pyrimidine (6.09 g, 21.6 mmol) from the previous step, 2.0 M aqueous sodium carbonate (56.5 mL) and Aliquat® 336 (728 mg, 1.80 mmol) in o-xylene (113 mL) was sparged with nitrogen for 30 minutes and tetrakis(triphenylphosphine)palladium(0) (520 mg, 0.45 mmol) was added and the mixture was heated at reflux for 42 h. After cooling to room temperature the mixture was vacuum filtered to remove the solids which were rinsed with water and toluene (50 mL each). The collected precipitate was crystallized by dissolving in hot chlorobenzene (600 mL), reducing the volume by approximately half and then slowly adding isopropanol (200 mL) and letting stand at room temperature overnight. The crystals were collected by gravity filtration, rinsing with isopropanol. The crystals were then triturated with hot isopropanol (200 mL) for 2 h, then filtered and dried under high vacuum to give 3,9-dimethyl-1,7-bis(3-pyrimidin-2-ylphenyl)-4,10-diazachrysene (2.11 g, 41% yield) as a white solid with 99.9% purity by UPLC. The structure was confirmed by $^1$H NMR spectroscopy of a sample dissolved in deuteriotetrahydrofuran. The product was subjected to vapor sublimation as a final purification step.

Synthesis Example 3

This example illustrates the synthesis of Compound 5,3,9-dimethyl-1,7-bis[3-(3-pyridyl)phenyl]-4,10-diazachrysene.

Step 1:

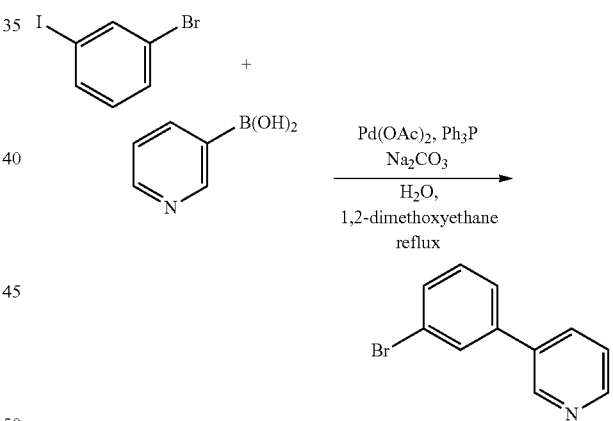

A mixture of 3-bromoiodobenzene (10.8 g, 70.0 mmol, pyridine-3-borononic acid (8.6 g, 70.0 mmol) in 1,2-dimethoxyethane (315 mL) and 2.0 M aqueous sodium carbonate (105 mL) was sparged with nitrogen for 30 minutes, then palladium acetate (393 mg, 1.75 mmol) and triphenylphosphine (918 mg, 3.50 mmol) were added and the mixture was heated at reflux for 18 h. The reaction mixture was cooled to room temperature and extracted with ethyl acetate (3×150 mL). The combined organic layer was washed with water and brine (2×150 mL each), then dried over magnesium sulfate, filtered and concentrated to a dark brown oil. The crude product was purified by silica gel MPLC (0-90% ethyl acetate in hexanes as eluent). The product fractions eluting when the gradient had reached 55-85% ethyl acetate in hexanes were combined and concentrated by rotary evaporation to give 3-(3-bromophenyl)pyridine as a dark yellow oil (14.5 g, 88% yield) having a purity of 97% based on UPLC analysis. This material was taken directly to Step 2.

Step 2:

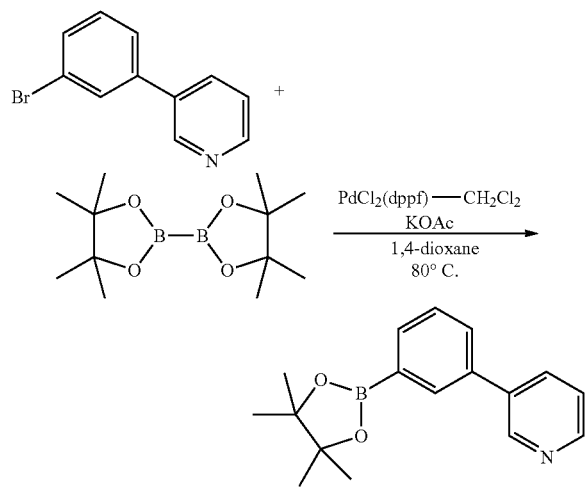

A mixture of 3-(3-bromophenyl)pyridine (14.5 g, 61.9 mmol) from the previous step, bis(pinacolato)diboron (18.9 g, 74.3 mmol) and potassium acetate (18.2 g, 185 mmol) in dry 1,4-dioxane (477 mL) was sparged with nitrogen for 15 minutes and then [1,1-bis(diphenylphosphino)ferrocene]palladium(II) chloride, complex with dichloromethane (1:1) (1.52 g, 1.86 mmol) was added and nitrogen sparge was continued for another 10 minutes after which the mixture was heated at reflux overnight 18 h. After cooling to room temperature, the crude reaction mixture was poured over a pad of silica gel and eluted first with toluene and then with 1/1 ethyl acetate/hexanes. The combined filtrate was concentrated to a dark brown oil by rotary evaporation and purified by silica gel MPLC (10-100% ethyl acetate in hexanes as eluent). The fractions eluting at 30-65% ethyl acetate in hexanes were combined to give, after concentration by rotary evaporation and drying under hi-vacuum, 3-[3-(4,4,5,5-tetramethyl-1,3,2-dioxaborolan-2-yl)phenyl]pyridine (17.3 g, 99.3% yield), as an off-white solid.

Step 3:

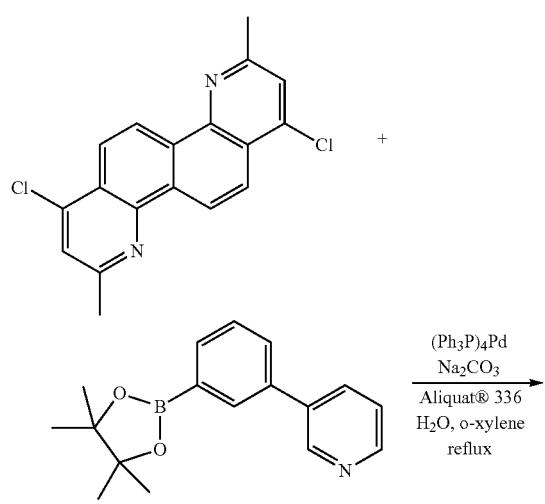

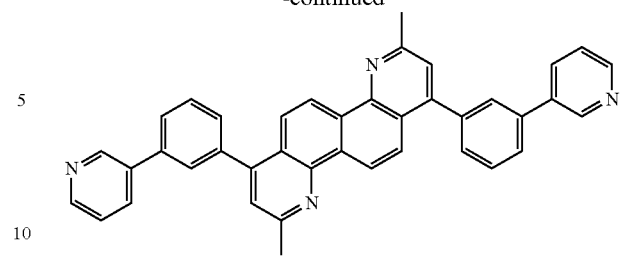

A mixture of 1,7-dichloro-3,9-dimethyl-4,10-diazachrysene (2.94 g, 9.00 mmol) from the Step 3 of Synthesis Example 1, 3-[3-(4,4,5,5-tetramethyl-1,3,2-dioxaborolan-2-yl)phenyl]pyridine (6.07 g, 21.6 mmol) from the previous step, 2.0 M aqueous sodium carbonate (56.5 mL) and Aliquat® 336 (728 mg, 1.80 mmol) in o-xylene (113 mL) was sparged with nitrogen for 30 minutes and tetrakis(triphenylphosphine)palladium(0) (520 mg, 0.45 mmol) was added and the mixture was heated at reflux for 18 h. After cooling to room temperature the mixture was vacuum filtered to remove the solids which were rinsed with water and toluene (50 mL each). After drying under high vacuum, the off-white solid was purified by continuous extraction with refluxing toluene through a 3 cm (diameter)×9 cm (height) extraction thimble charged with a plug of silica gel in a modified soxhlet extraction apparatus having a frit bottom in the extraction chamber. After 2 days of continuous extraction the toluene extract was cooled to room temperature and the precipitate was collected by filtration to give 3,9-dimethyl-1,7-bis[3-(3-pyridyl)phenyl]-4,10-diazachrysene (3.91 g, 77% yield) as a powdery, white solid with 99.8% purity by UPLC. The structure was confirmed by $^1$H NMR spectroscopy of a sample dissolved in deuteriotetrahydrofuran. The product was subjected to vapor sublimation as a final purification step.

Comparative Compound A

Comparative Compound A was prepared using a procedure similar to Synthesis Example 3.

Comparative Compound A

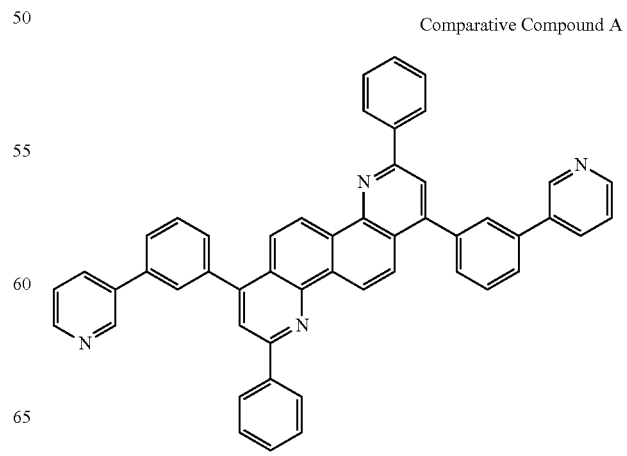

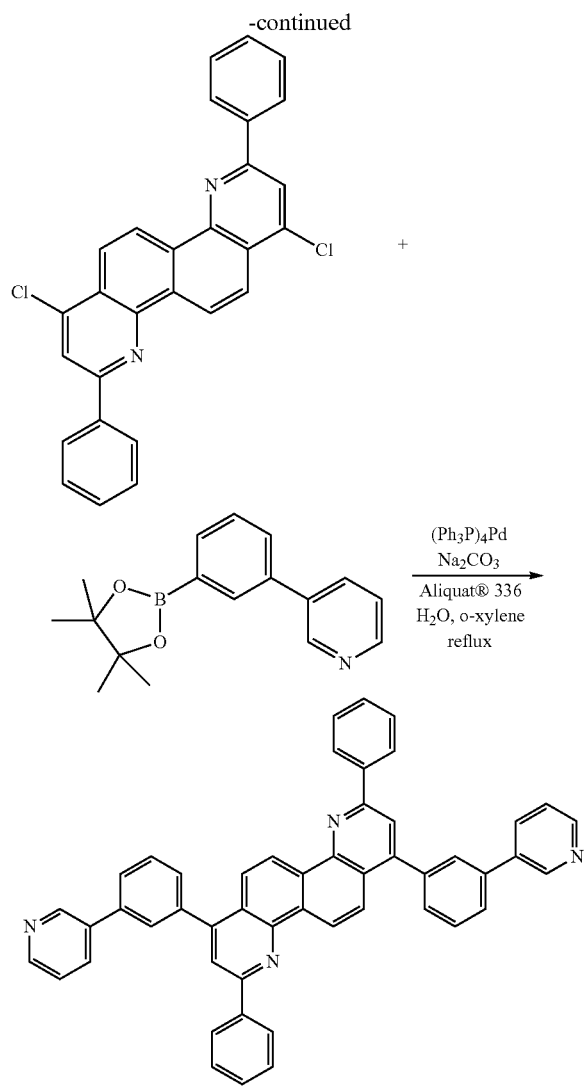

A mixture of 1,7-dichloro-3,9-diphenyl-4,10-diazachrysene (6.77 g, 15.0 mmol; prepared according to the procedure provided in WO2012082593), 3-[3-(4,4,5,5-tetramethyl-1,3,2-dioxaborolan-2-yl)phenyl]pyridine, (10.1 g, 36.0 mmol; prepared as described in Step 2 of Synthesis Example 3), 2.0 M aqueous sodium carbonate (94.0 mL) and Aliquat® 336 (1.21 g, 3.00 mmol) in o-xylene (188 mL) was sparged with nitrogen for 30 minutes.

Tetrakis(triphenylphosphine)palladium(0) (867 mg, 0.75 mmol) was added and the mixture was heated at reflux for 18 h. After cooling to room temperature the bi-layer reaction mixture was filtered and the crude solid was washed with water and toluene (approximately 50 mL each). The crude gray solid was purified by continuous extraction with refluxing toluene (2×300 mL) in a modified soxhlet extraction apparatus as described in Step 3 of Synthesis Example 3. The precipitated white solid from both toluene extracts was collected by filtration, washed with isopropanol (approximately 50 mL) and dried under high-vacuum overnight. UPLC analysis of this material indicated that it contained 2.3% of mono-substituted intermediate, 1-chloro-7-[3'-(3"-pyridyl)-1'-phenyl]-3,9-diphenyl-4,10-diazachrysene. The dried solid was re-subjected to the reaction conditions as described above for 36 hours and the crude solid isolated from the reaction mixture was dissolved in trifluoroacetic acid (30 mL). An insoluble black residue was removed by filtration and the filtrate was concentrated to ⅕ of its original volume and diluted with dichloromethane (approximately 50 mL). Aqueous 6.25 M NaOH (approximately 30 mL) was added in portions and a precipitate formed. The white precipitate was isolated by filtration, washed with water (approximately 200 mL) and isopropanol (approximately 200 mL), and triturated with toluene (approximately 300 mL). The solid was gravity filtered, rinsing with toluene and isopropanol (approximately 50 mL each), and drying under high-vacuum overnight to give 3,9-diphenyl-1,7-bis-[3'-(3"-pyridyl)-1'-phenyl]-4,10-diazachrysene (6.63 g, 60% yield) as a white solid with 99.9% purity by UPLC. The structure was confirmed by $^1$H NMR spectroscopy of a sample dissolved in trifluoroacetic acid-d. The product was subjected to vapor sublimation as a final purification step.

Device Examples (a) Materials

HIJ-1 is an electrically conductive polymer doped with a polymeric fluorinated sulfonic acid. Such materials have been described in, for example, published U.S. patent applications US 2004/0102577, US 2004/0127637, US 2005/0205860, and published PCT application WO 2009/018009.
HT-1 is a copolymer of a triarylamine and a fluorene.
HT-2 is a triarylamine-containing polymer.
Host-1 is an aryl-anthracene.
Dopant-1 is a diarylamino-substituted chrysene.
EIJ-1 is a metal quinolate compound.

(b) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a toluene solution of HT-1, heated to remove solvent, cooled, and exposed to deep UV radiation. The substrates were then rinsed with anisole, dried, and spin-coated with a toluene solution of HT-2, and then heated to remove solvent. After cooling the substrates were spin-coated with a methyl benzoate solution of the host(s) and dopant, and heated to remove solvent. The substrates were masked and placed in a vacuum chamber. The electron transport layer was deposited by thermal evaporation, followed by a layer of EIJ-1. Masks were then changed in vacuo and a layer of Al was deposited by thermal evaporation. The chamber was vented, and the devices were encapsulated using a glass lid, dessicant, and UV curable epoxy.

(c) Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

Device Example 1 and Comparative Example A

This example illustrates the use of a compound having Formula I as the electron transport material in a device.

The device had the following structure on a glass substrate:
anode=Indium Tin Oxide ("ITO") (50 nm)
hole injection layer=HIJ-1 (50 nm)
first hole transport layer=HT-1 (20 nm)
second hole transport layer=HT-2 (14 nm)
photoactive layer=93:7 (weight ratio) Host-1:Dopant-1 (40 nm);
electron transport layer=shown below (10 nm)
electron injection layer/cathode=EIJ-1/Al (3.5/100 nm)
The results are given in Table 1 below.

TABLE 1

| Device Results | | | | | |
|---|---|---|---|---|---|
| Electron Transport Layer | C.E. cd/A | EQE (%) | CIEX | CIEY | V at 15 mA/cm² |
| Comparative A | 5.0 | 5.7 | 0.141 | 0.099 | 5.0 |
| Compound 5 | 6.6 | 7.1 | 0.139 | 0.107 | 3.9 |

All data at 1000 nits, unless otherwise specified.
CE = current efficiency;
EQE = external quantum efficiency;
CIEx and CIEy are the x and y color coordinates according to the C.I.E. chromaticity scale (Commission Internationale de L'Eclairage, 1931).

It can be seen from Table 1, that the device with Compound 5 had higher efficiency and lower voltage that the device with Comparative Compound A Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula I

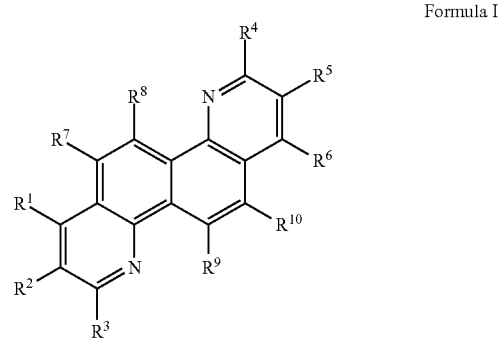

Formula I wherein:
$R^1$-$R^{10}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring;

with the proviso that (i) at least one of $R^1$-$R^3$ and at least one of $R^4$-$R^6$ is selected from the group consisting of alkyl, alkoxy, silyl, and deuterated analogs thereof, and (ii) at least one of $R^1$-$R^3$ and at least one of $R^4$-$R^6$ is selected from the group consisting of aryl, aryloxy, and deuterated analogs thereof, and wherein at least one of $R^1$-$R^3$ is an aryl group having Formula a

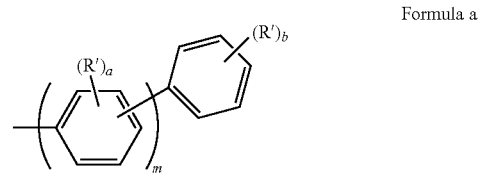

Formula a where:
R' is the same or different at each occurrence and is selected from the group consisting of D, alkyl, alkoxy, aryl, aryloxy, silyl, diarylamino, deuterated alkyl, deuterated alkoxy, deuterated aryl, deuterated aryloxy, deuterated silyl, and deuterated diarylamino;

a is the same or different at each occurrence and is an integer from 0-4;

b is an integer from 0-5; and m is an integer from 1 to 5.

2. A compound having Formula I

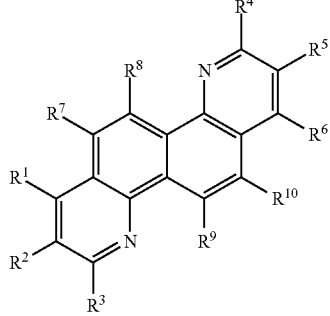
Formula I

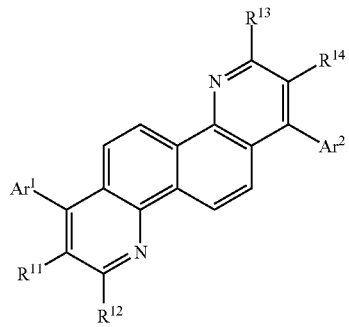
Formula I(a)

wherein:

$R^1$-$R^{10}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring;

with the proviso that (i) at least one of $R^1$-$R^3$ and at least one of $R^4$-$R^6$ is selected from the group consisting of alkyl, alkoxy, silyl, and deuterated analogs thereof, and (ii) at least one of $R^1$-$R^3$ and at least one of $R^4$-$R^6$ is selected from the group consisting of aryl, aryloxy, and deuterated analogs thereof, and wherein at least one of $R^4$-$R^6$ is an aryl group having Formula a

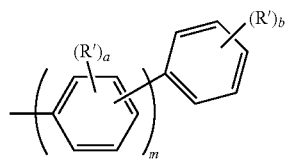
Formula a where:

R' is the same or different at each occurrence and is selected from the group consisting of D, alkyl, alkoxy, aryl, aryloxy, silyl, diarylamino, deuterated alkyl, deuterated alkoxy, deuterated aryl, deuterated aryloxy, deuterated silyl, and deuterated diarylamino;

a is the same or different at each occurrence and is an integer from 0-4;

b is an integer from 0-5; and m is an integer from 1 to 5.

3. A compound selected from the group consisting of a compound having Formula I(a) and a compound having Formula I(c)

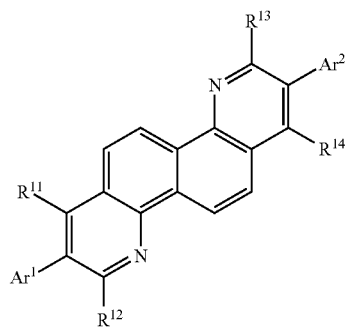
Formula I(c)

wherein:

$Ar^1$ and $Ar^2$ are the same or different and are selected from the group consisting of aryl, aryloxy, and deuterated analogs thereof;

$R^{11}$-$R^{14}$ are the same or different and are selected from the group consisting of H, D, alkyl, aryl, alkoxy, aryloxy, silyl, deuterated analogs of alkyl, aryl, and deuterated silyl, where adjacent R groups can be joined together to form a ring; and all other sites are H or D;

with the proviso that at least one of $R^{11}$ and $R^{12}$ and at least one of $R^{13}$ and $R^{14}$ is selected from the group consisting of alkyl, alkoxy, silyl, and deuterated analogs thereof.

4. The compound of claim 3, wherein $Ar^1$ includes a heteroaryl or deuterated heteroaryl group.

5. The compound of claim 4, wherein the heteroaryl or deuterated heteroaryl group is derived from a compound selected from the group consisting of pyridine, pyrimidine, triazine, diazole, benzodiazole, quinoxaline, carbazole, and deuterated analogs thereof.

6. The compound of claim 3, wherein $Ar^2$ includes a heteroaryl or deuterated heteroaryl group.

7. The compound of claim 6, wherein the heteroaryl or deuterated heteroaryl group is derived from a compound selected from the group consisting of pyridine, pyrimidine, triazine, diazole, benzodiazole, quinoxaline, carbazole, and deuterated analogs thereof.

8. The compound of claim 3, wherein the compound is selected from the group consisting of Compound 1
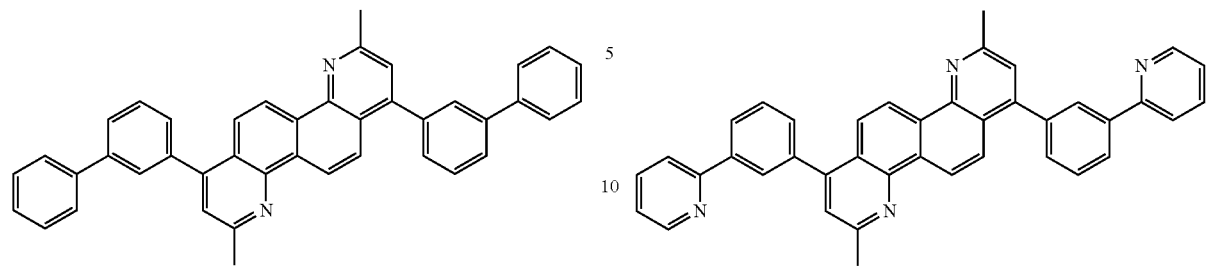
Compound 2
Compound 3
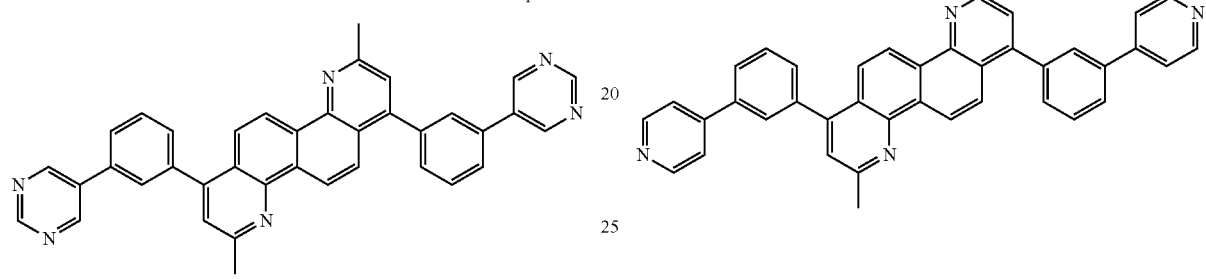
Compound 4
Compound 5
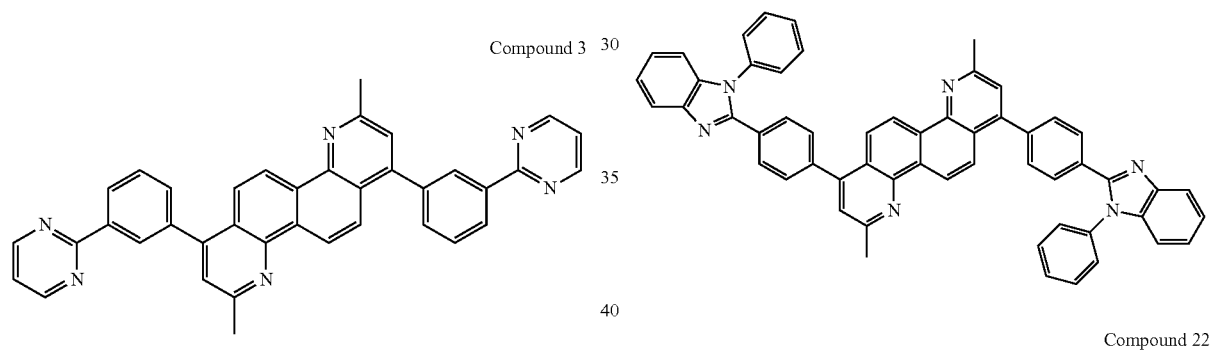
Compound 6
Compound 7
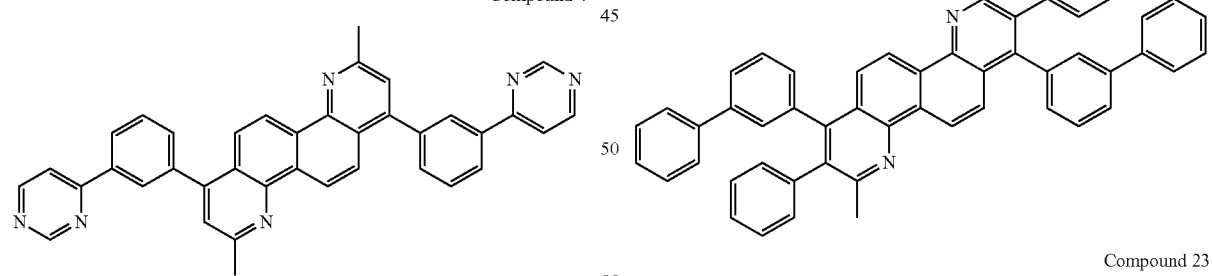
Compound 8
Compound 22
Compound 23
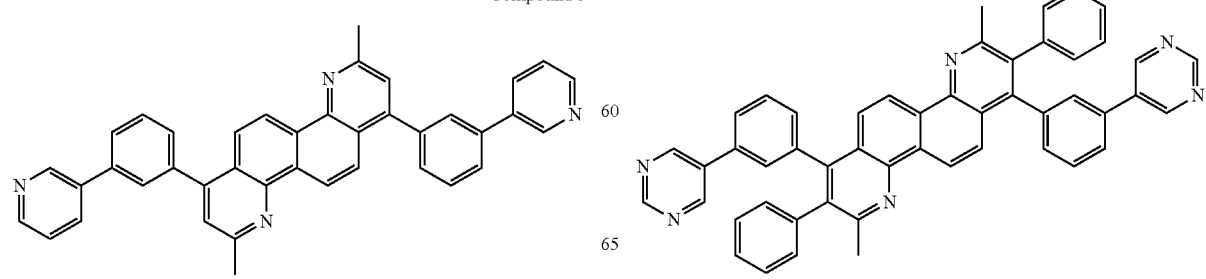

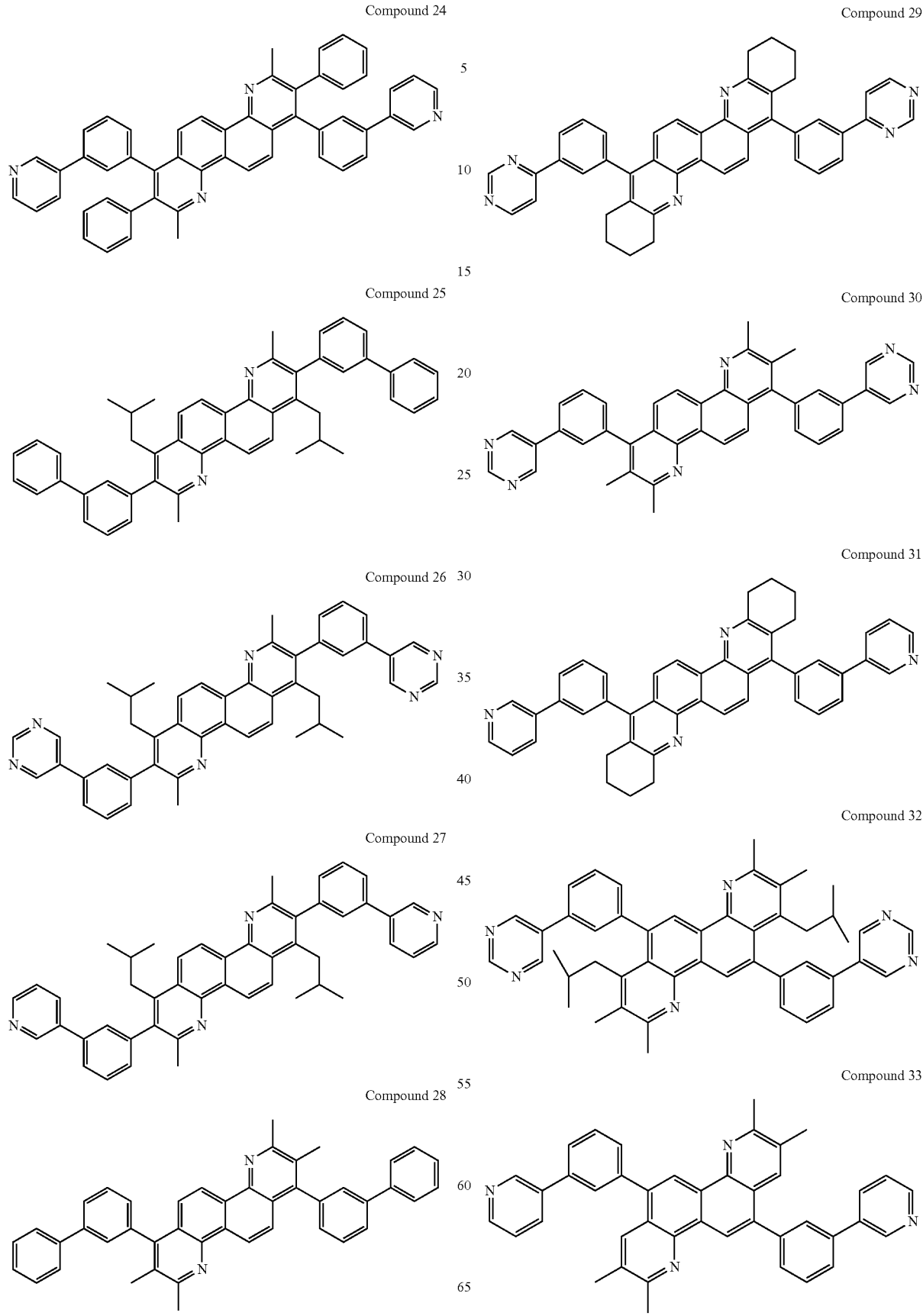

Compound 34

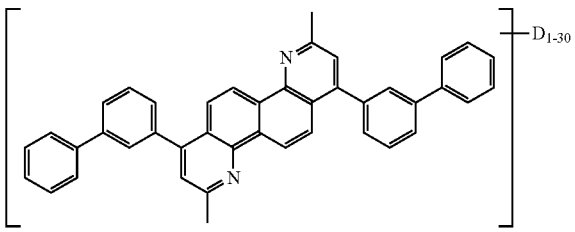

Compound 35

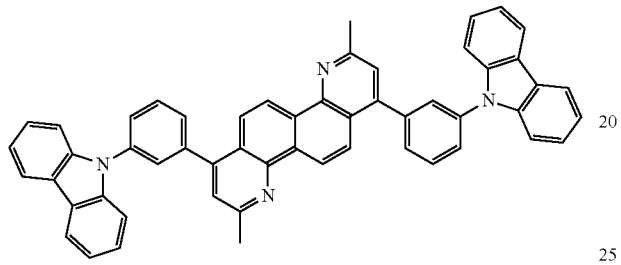

Compound 36

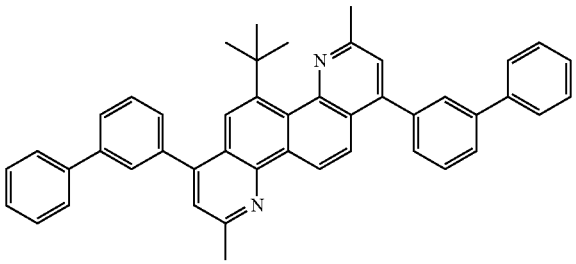

Compound 37

Compound 38

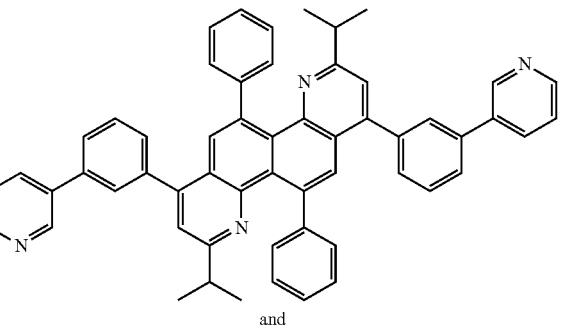

and

Compound 39

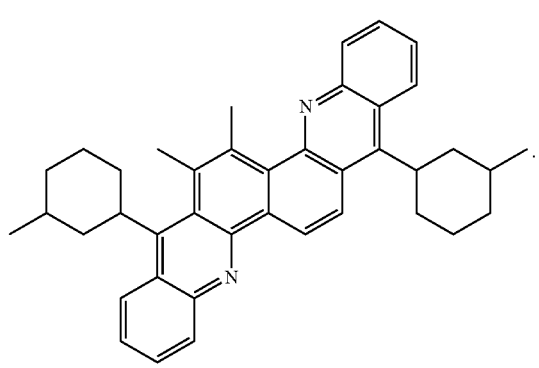

9. A composition comprising
(a) a host compound according to claim 6; and
(b) a dopant capable of electroluminescence having an emission maximum between 380 and 750 nm.

10. An electronic device comprising at least one electroactive layer positioned between two electrical contact layers, wherein the at least one electroactive layer of the device includes the compound of claim 1.

11. An electronic device comprising at least one electroactive layer positioned between two electrical contact layers, wherein the at least one electroactive layer of the device includes the compound of claim 2.

12. An electronic device comprising at least one electroactive layer positioned between two electrical contact layers, wherein the at least one electroactive layer of the device includes the compound of claim 3.

13. The electronic device of claim 12, wherein the at least one layer is an electron transport layer.

14. The electronic device of claim 12, wherein the at least one layer is a photoactive layer.

* * * * *